United States Patent
Papeo et al.

(10) Patent No.: US 9,422,243 B2
(45) Date of Patent: Aug. 23, 2016

(54) 3-PHENYL-ISOQUINOLIN-1(2H)-ONE DERIVATIVES AS PARP-1 INHIBITORS

(71) Applicant: NERVIANO MEDICAL SCIENCES S.R.L., Nerviano (IT)

(72) Inventors: Gianluca Mariano Enrico Papeo, Cernusco Lombardone (IT); Alessandra Cirla, Varese (IT); Matteo D'Anello, Novate Milanese (IT); Alessandra Scolaro, Bresso (IT); Fabio Zuccotto, Milan (IT)

(73) Assignee: NERVIANO MEDICAL SCIENCES S.R.L. a corporation, Nerviano (MI) (IT)

( * ) Notice: Subject to any disclaimer, the term of this patent is extended or adjusted under 35 U.S.C. 154(b) by 0 days.

(21) Appl. No.: 14/358,537

(22) PCT Filed: Nov. 20, 2012

(86) PCT No.: PCT/EP2012/073125
§ 371 (c)(1),
(2) Date: May 15, 2014

(87) PCT Pub. No.: WO2013/076090
PCT Pub. Date: May 30, 2013

(65) Prior Publication Data
US 2014/0336192 A1    Nov. 13, 2014

(30) Foreign Application Priority Data

Nov. 25, 2011 (EP) .................................. 11190687
Mar. 27, 2012 (EP) .................................. 12161489

(51) Int. Cl.
| | | |
|---|---|---|
| *C07D 401/10* | (2006.01) | |
| *C07D 405/04* | (2006.01) | |
| *C07D 217/24* | (2006.01) | |
| *A61K 31/472* | (2006.01) | |
| *A61K 31/4725* | (2006.01) | |
| *A61K 31/4188* | (2006.01) | |

(52) U.S. Cl.
CPC ............ *C07D 217/24* (2013.01); *C07D 401/10* (2013.01); *C07D 405/04* (2013.01); *A61K 31/4188* (2013.01); *A61K 31/472* (2013.01); *A61K 31/4725* (2013.01)

(58) Field of Classification Search
CPC ... C07D 401/10; C07D 405/04; C07D 217/24
See application file for complete search history.

(56) References Cited

U.S. PATENT DOCUMENTS 8,592,416 B2 * 11/2013 Papeo et al. ................. 514/235.2
8,993,594 B2 * 3/2015 Papeo et al. .................... 514/309

FOREIGN PATENT DOCUMENTS

| EP | 1 396 488 A1 | 3/2004 |
| EP | 1 544 194 A1 | 6/2005 |
| WO | 02090334 A1 | 11/2002 |
| WO | 2010133647 A1 | 11/2010 |
| WO | WO 2010133647 A1 * | 11/2010 |

OTHER PUBLICATIONS

Patani et al. Chem. Rev. 1996, 96, 3147-3176.*
International Search Report issued PCT Application No. PCT/EP2012/073125, 2012.

* cited by examiner

*Primary Examiner* — Matthew Coughlin
(74) *Attorney, Agent, or Firm* — Silvia Salvadori, P.C.; Silvia Salvadori

(57) ABSTRACT

There are provided substituted 3-phenyl-isoquinolin-1(2H)-one derivatives which selectively inhibit the activity of poly (ADP-ribose) polymerase PARP-1 with respect to poly (ADP-ribose) polymerase PARP-2. The compounds of the present invention are therefore useful in treating diseases such as cancer, cardiovascular diseases, central nervous system injury and different forms of inflammation. The present invention also provides methods for preparing these compounds, pharmaceutical compositions comprising these compounds, and methods of treating diseases utilizing pharmaceutical compositions comprising these compounds.

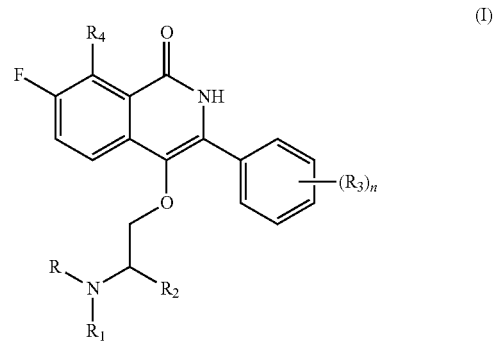

(I)

10 Claims, No Drawings

3-PHENYL-ISOQUINOLIN-1(2H)-ONE DERIVATIVES AS PARP-1 INHIBITORS

This application is a U.S. national stage of PCT/EP2012/073125 filed on Nov. 20, 2012, which claims priority to and the benefit of European Patent Application No. 12161489.5 filed on Mar. 27, 2012 and on European Patent Application No. 11190687.1, filed on Nov. 25, 2011.

The present invention concerns 3-phenyl-isoquinolin-1 (2H)-one derivatives which selectively inhibit the activity of poly (ADP-ribose) polymerase PARP-1 with respect to poly (ADP-ribose) polymerase PARP-2. The compounds of this invention are therefore useful in treating diseases such as cancer, cardiovascular diseases, central nervous system injury and different forms of inflammation. The present invention also provides methods for preparing these compounds, pharmaceutical compositions comprising these compounds, and methods of treating diseases utilizing pharmaceutical compositions comprising these compounds.

Poly (ADP-ribose) polymerases belong to a family of 18 members that catalyze the addition of ADP-ribose units to DNA or different acceptor proteins, which affect cellular processes as diverse as replication, transcription, differentiation, gene regulation, protein degradation and spindle maintenance. PARP-1 and PARP-2 are the only enzymes among the PARPs that are activated by DNA damage and are involved in DNA repair.

PARP-1 is a nuclear protein consisting of three domains: the N-terminal DNA-binding domain containing two zinc fingers, the auto modification domain, and the C-terminal catalytic domain. PARP-1 binds through the zinc-finger domain to DNA single strand breaks (SSB), cleaves $NAD^+$, and attaches multiple ADP-ribose units to target proteins such as histones and various DNA repair enzymes. This results in a highly negatively charged target, which in turn leads to the unwinding and repair of the damaged DNA through the base excision repair pathway. In knock out mouse models, deletion of PARP-1 impairs DNA repair but it is not embryonic lethal. Double knock out PARP-1 and PARP-2 mice instead die during early embryogenesis, suggesting that the two enzymes display not completely overlapping functions. Enhanced PARP-1 expression and/or activity have been shown in different tumor cell lines, including malignant lymphomas, hepatocellular carcinoma, cervical carcinoma, colorectal carcinoma, leukemia. This may allow tumor cells to withstand genotoxic stress and increase their resistance to DNA-damaging agents. As a consequence, inhibition of PARP-1 through small molecules has been shown to sensitize tumor cells to cytotoxic therapy (e.g. temozolomide, platinums, topoisomerase inhibitors and radiation). A significant window seems to exist between the ability of a PARP inhibitor to potentiate therapeutic benefits and undesirable side effects. Whereas the therapeutic use of PARP inhibitors in combination with DNA damaging agents is not novel, the use of these agents as monotherapy, in particular tumor genetic backgrounds deficient in the homologous recombination DNA repair, represents a new approach. Individuals with heterozygous germ line mutations in either the BRCA-1 or BRCA-2 homologous recombination repair genes exhibit high life time risks of developing breast and other cancers. Tumors arising in mutation carriers have generally lost the wild type allele and do not express functional BRCA-1 and BRCA-2 proteins.

Therefore, loss of these two proteins leads to a tumor-specific dysfunction in the repair of double strand breaks by homologous recombination. It is known that when PARP-1 is inhibited, base excision repair is reduced and single strand breaks that are generated during the normal cell cycle persist. It has also been established that replication forks that encounter an unrepaired break can form double strand breaks which are normally repaired by homologous recombination. Tumor cells that are deficient in homologous recombination repair such as BRCA-1 and BRCA-2 mutants are therefore highly sensitive to PARP inhibition compared with wild-type cells. This is in line with the concept of synthetic lethality, in which the two pathway defects alone are innocuous but combined become lethal: PARP inhibitors may be more effective in patients with tumors with specific DNA repair defects without affecting normal heterozygous tissues. Putative patient population includes, besides BRCA mutants that represent the majority of hereditary breast and ovarian cancer, also a substantial fraction of sporadic cancers with defects in homologous recombination repair, a phenomenon termed "BRCAness". For example, methylation of the promoters of the BRCA-1 or FANCF genes and amplification of the EMSY gene, which encodes a BRCA-2 interacting protein. By extending the rational of synthetic lethality of PARP and BRCA-1 and BRCA-2, it is likely that deficiencies in any gene that is not redundant in double strand break repair should be sensitive to PARP inhibition. For example, ATM deficiency, found in patients with T-cell prolymphocytic leukemia and B-cell chronic lymphocytic leukemia and breast cancer and CHK2 germ line mutations identified in sarcoma, breast cancer, ovarian cancer and brain tumors, have also been shown to be synthetically lethal in combination with PARP deficiency as well as deficiencies in other known HR pathway proteins (including RAD51, DSS1, RAD54, RPA1, NBS1, ATR, CHK1, CHK2, FANCD2, FANCA, FANCC and pTEN). Mutations in FANCC and FANCG have been shown in pancreatic cancer. Methylation of FANCF promoter has been found in ovarian, breast, cervical, lung carcinomas. The first clinical evidence that BRCA-mutated cancer may be sensitive to PARP inhibitor monotherapy comes from the phase I trial of the oral, small molecule PARP inhibitor Olaparib. In an enriched phase I population for BRCA mutation carriers, an objective response rate of 47% were observed in 19 patients with BRCA mutations and breast, ovarian and prostate cancer. Other PARP inhibitors, such as Rucaparib and Veliparib are currently known to be in phase II clinical trials in combination as well as single agent. Early indications are that these therapies show low toxicity as single agent. Anyway compounds with high selectivity on PARP-1 are expected to show even less toxicity in view of a chronic treatment schedule or in combination.

PARP-1 has also been implicated in angiogenesis. In particular, PARP-1 inhibition seems to result in decreased accumulation of the transcription hypoxia-inducible factor 1α, an important regulator of tumor cell adaptation to hypoxia.

Pro-inflammatory stimuli trigger the release of pro-inflammatory mediators that induce the production of peroxynitrate and hydroxyl radicals, which in turn yield to DNA single strand breakage with consequent activation of PARP-1. Over activation of PARP-1 results in depletion of NAD+ and energy stores, culminating in cell dysfunction and necrosis. This cellular suicide mechanism has been implicated in the pathomechanism of stroke, myocardial ischemia, diabetes, diabetes-associated cardiovascular dysfunction, shock, traumatic central nervous system injury, arthritis, colitis, allergic encephalomyelitis and various other forms of inflammation. Of special interest is the enhancement by PARP-1 of nuclear factor kB-mediated transcription, which plays a central role in the expression of inflammatory cytokines, chemokines and inflammatory mediators.

In a study on nitrogen heterocycles in the Journal of the Chemical Society, Perkin Transactions 1, (1977), (9), 959-65, 3-phenyl-1(2H)-isoquinolinones are described. Isoquinolin-1(2H)-ones with pharmacological activity are described in Science of Synthesis (2005), 15, 839-906. Some patent applications describe isoquinoline derivatives for the treatment of glaucoma, EP389995, and of arteriosclerosis and hyperlipoproteinemia, EP591937. WO2002090334 in the name of KUDOS PHARM describes isoquinolinone derivatives used for inhibiting the PARP activity. WO2008092292 describes a method of treating pathological condition associated with a melatonin receptor using 2-substituted (2H)-isoquinolinones. WO2010133647 describes 1(2H)-isoquinolinones active as PARP-1 inhibitors, in the name of Nerviano Medical Sciences. Some specific compounds of the aforementioned WO2010133647 are excluded from the present general formula.

The present invention provides new 3-phenyl-isoquinolin-1(2H)-one derivatives which are endowed with selective inhibition activity to PARP-1 with respect to PARP-2 and are thus useful in therapy of cancer, cardiovascular diseases, nervous system injury and inflammation.

Accordingly, a first object of the present invention is to provide a compound of formula (I):

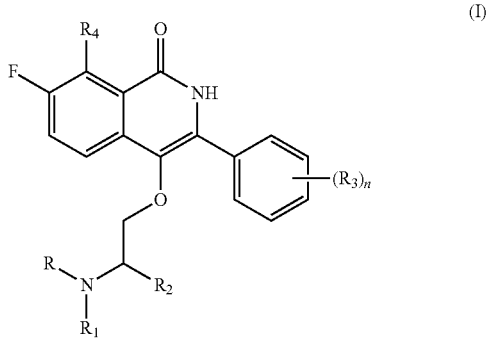

(I)

wherein R and $R_1$ are independently hydrogen or an optionally substituted group selected from linear or branched $C_1$-$C_6$ alkyl, $C_3$-$C_7$ cycloalkyl and heterocyclyl, or, taken together with the nitrogen atom to which they are bonded, form an optionally substituted heterocycle;

$R_2$ is hydrogen or an optionally substituted group selected from linear or branched $C_1$-$C_6$ alkyl and $C_3$-$C_7$ cycloalkyl;

$R_3$ is fluorine, chlorine, bromine, cyano, or an optionally substituted group selected from linear or branched $C_1$-$C_6$ alkyl, $C_1$-$C_6$ alkoxy, polyfluorinated $C_1$-$C_6$ alkyl, polyfluorinated $C_1$-$C_6$ alkoxy, heterocyclyl, aryloxy, arylamino, $C_1$-$C_6$ alkylsulphonyl; or $R_3$ may be represented by a dioxolyl, dioxinyl or dioxepinyl ring, fused with the phenyl ring;

$R_4$ is hydrogen or fluorine, and
when $R_4$ is hydrogen, n is a number between 1 and 5;
when $R_4$ is fluorine, n is a number between 0 and 5;
or an optical isomer, tautomer, or a pharmaceutically acceptable salt thereof;
with the exception of the following compounds:
4-(2-amino-ethoxy)-3-(3-chloro-phenyl)-7-fluoro-2H-isoquinolin-1-one,
4-(2-amino-ethoxy)-7-fluoro-3-(4-phenoxy-phenyl)-2H-isoquinolin-1-one,
4-(2-amino-ethoxy)-7-fluoro-3-(3-methoxy-phenyl)-2H-isoquinolin-1-one and
4-(2-amino-ethoxy)-7-fluoro-3-(4-methoxy-phenyl)-2H-isoquinolin-1-one.

The present invention also provides methods of synthesizing the 3-phenyl-isoquinolin-1(2H)-one derivatives of formula (I) as defined above through a process consisting of standard synthetic transformations.

As stated above, we have discovered that compounds of formula (I) as defined above are potent and selective PARP-1 inhibitors with respect to PARP-2 and are thus useful in the treatment of cancer, cardiovascular diseases, nervous system injury and for anti-inflammation therapy. Therefore, the present invention also provides a method for treating diseases mediated by PARP-1 protein, which comprises administering to a mammal in need thereof, preferably a human, an effective amount of a compound of formula (I), as defined above.

A preferred method of the present invention is to treat a disease mediated by PARP-1 protein selected from the group consisting of cancer, cardiovascular diseases, nervous system injury and inflammation.

Another preferred method of the present invention is to treat specific types of cancer including, but not limited to, carcinoma, such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkitt's lymphoma; hematopoietic tumors of myeloid lineage, including acute and chronic myelogenous leukemia, myelodysplastic syndrome and promyelocytic leukemia; tumors of mesenchymal origin, including fibrosarcoma, Ewing's sarcoma and rhabdomyosarcoma; tumors of the central and peripheral nervous system, including astrocytoma neuroblastoma, glioma, glioblastoma and schwannoma; other tumors, including melanoma, seminoma, teratocarcinoma, osteosarcoma, xeroderma pigmentosum, keratoxanthoma, thyroid follicular cancer and Kaposi's sarcoma.

In addition, the method of the present invention also provides tumor angiogenesis and metastasis inhibition.

Another preferred method of the present invention is to treat specific types of cardiovascular diseases including, but not limited to, myocardial reperfusion injury, cardiomyopathy and diabetic cardiovascular dysfunction.

Another preferred method of the present invention is to treat specific types of central nervous system injury including, but not limited to, stroke, brain injury and neurodegenerative disorders.

Another preferred method of the present invention is to treat specific types of inflammation diseases including, but not limited to, colitis, arthritis, and uveitis.

The present invention further provides an in vitro method for selectively inhibiting PARP-1 protein activity which comprises contacting the said protein with an effective amount of a compound of formula (I), as defined above.

Moreover the present invention provides a method of treatment comprising a compound of formula (I) in combination with radiation therapy or chemotherapy regimen for simultaneous, separate or sequential use in anticancer therapy.

The present invention also provides a pharmaceutical composition comprising a therapeutically effective amount of a compound of formula (I) or a pharmaceutically acceptable salt thereof, and at least one pharmaceutically acceptable excipient, carrier or diluent.

In addition to a compound of formula (I), the pharmaceutical composition of the present invention may further comprise one or more chemotherapeutic—e.g. cytostatic or cytotoxic—agents, antibiotic-type agents, alkylating agents, antimetabolite agents, hormonal agents, immunological agents, interferon-type agents, cyclooxygenase inhibitors (e.g. COX-2 inhibitors), matrix metalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like. Preferably, the chemotherapeutic agent is an alkylating agent. Even more preferably, the alkylating agent is temozolomide.

Additionally, the invention provides a product comprising a compound of formula (I) or a pharmaceutically acceptable salt thereof, as defined above, and one or more chemotherapeutic agents, as a combined preparation for simultaneous, separate or sequential use in anticancer therapy. Preferably, the chemotherapeutic agent is an alkylating agent. Even more preferably, the alkylating agent is temozolomide.

In yet another aspect, the invention provides a compound of formula (I) or a pharmaceutically acceptable salt thereof, as defined above, for use as a medicament, preferably as a medicament with anticancer activity.

Moreover, the invention provides a compound of formula (I) or a pharmaceutically acceptable salt thereof, as defined above, for use in a method of treating a disease mediated by PARP-1 protein, preferably cancer, cardiovascular diseases, nervous system injury and inflammation.

Finally, the invention provides the use of a compound of formula (I) or a pharmaceutically acceptable salt thereof, as defined above, in the manufacture of a medicament for treating a disease mediated by PARP-1 protein.

The present invention also provides methods of synthesizing the substituted derivatives of formula (I) prepared through a process consisting of standard synthetic transformations.

If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

The term "pharmaceutically acceptable salt" of compounds of formula (I) refers to those salts that retain the biological effectiveness and properties of the parent compound. Such salts include acid addition salts with inorganic acids such as hydrochloric, hydrobromic, nitric, phosphoric, sulfuric, perchloric acid and the like, or with organic acids such as acetic, ascorbic, trifluoroacetic, propionic, glycolic, (D) or (L) lactic, (D) or (L) malic, oxalic, fumaric, maleic, methanesulphonic, ethanesulphonic, benzoic, p-toluenesulphonic, salicylic, cinnamic, mandelic, tartaric, citric, succinic, isethionic and malonic acid.

Pharmaceutically acceptable salts of the compounds of formula (I) also include the salts with inorganic or organic bases, e.g., alkali or alkaline-earth metals, especially sodium, potassium, calcium, ammonium or magnesium hydroxides, carbonates or bicarbonates, acyclic or cyclic amines, preferably methylamine, ethylamine, diethylamine, triethylamine, piperidine and the like.

Unless otherwise specified, when referring to the compounds of formula (I) per se as well as to any pharmaceutical composition thereof or to any therapeutic treatment comprising them, the present invention includes all of the isomers, tautomers, hydrates, solvates, complexes, carriers, N-oxides and pharmaceutically acceptable salts of the compounds of this invention.

In cases wherein compounds may exist in tautomeric forms, such as keto-enol tautomers, each tautomeric form is contemplated as being included within this invention whether existing in equilibrium or predominantly in one form.

With the term "halogen" we intend a fluorine, chlorine, bromine or iodine atom.

With the term "linear or branched $C_1$-$C_6$ alkyl", we intend any of the groups such as, for instance, methyl, ethyl, n-propyl, isopropyl, n-butyl, isobutyl, tert-butyl, sec-butyl, n-pentyl, n-hexyl, and the like.

With the term "$C_2$-$C_6$ alkenyl" we intend an aliphatic $C_2$-$C_6$ hydrocarbon chain containing at least one carbon-carbon double bond which can be linear or branched. Representative examples include, but are not limited to, ethenyl, 1-propenyl, 2-propenyl, 1- or 2-butenyl, and the like.

With the term "$C_2$-$C_6$ alkynyl" we intend an aliphatic $C_2$-$C_6$ hydrocarbon chain containing at least one carbon-carbon triple bond and which can be linear or branched. Representative examples include, but are not limited to, ethynyl, 1-propynyl, 2-propynyl, 1- or 2-butynyl, and the like.

With the term "linear or branched $C_1$-$C_6$ alkoxy", we intend any of the groups such as, for instance, methoxy, ethoxy, n-propoxy, isopropoxy, n-butoxy, isobutoxy, tert-butoxy, sec-butoxy, n-pentoxy, n-hexoxy, and the like.

With the term "$C_3$-$C_7$ cycloalkyl" we intend, unless otherwise provided, a 3- to 7-membered all-carbon monocyclic ring, which may contain one or more double bonds but does not have a completely conjugated π-electron system.

Examples of cycloalkyl groups, without limitation, are cyclopropane, cyclobutane, cyclopentane, cyclopentene, cyclohexane, cyclohexene and cyclohexadiene.

With the term "heterocyclyl" we intend a 3- to 8-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated π-electron bond system. Non limiting examples of such aryl groups are phenyl, α- or β-naphthyl or biphenyl groups.

The term "heteroaryl" as used herein refers to aromatic heterocyclic rings, typically 5- to 8-membered heterocycles with from 1 to 3 heteroatoms selected among N, O or S; the heteroaryl ring can be optionally further fused or linked to aromatic and non-aromatic carbocyclic and heterocyclic rings. Non limiting examples of such heteroaryl groups are, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, indazolyl, quinolinyl, isoquinolinyl, 1,2,3-triazolyl, 1-phenyl-1, 2,3-triazolyl, 2,3-dihydroindolyl, 2,3-dihydrobenzofuranyl, 2,3-dihydrobenzothiophenyl, benzopyranyl, 2,3-dihydrobenzoxazinyl, 2,3-dihydroquinoxalinyl and the like.

With the term "cyano" we intend a —CN residue.

With the term "nitro" we intend a —NO$_2$ group.

With the term "alkenyl" or "alkynyl" we intend any of the aforementioned straight or branched C$_2$-C$_6$ alkyl groups further bearing a double or triple bond. Non limiting examples of alkenyl or alkynyl groups of the invention are, for instance, vinyl, allyl, 1-propenyl, isopropenyl, 1-butenyl, 2-butenyl, 3-butenyl, 2-pentenyl, 1-hexenyl, ethynyl, 2-propynyl, 4-pentynyl, and the like.

With the term "polyfluorinated alkyl" or "polyfluorinated alkoxy" we intend any of the above linear or branched C$_1$-C$_6$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term "hydroxyalkyl" we intend any of the above C$_1$-C$_6$ alkyl, bearing an hydroxyl group such as, for instance, hydroxymethyl, 2-hydroxyethyl, 3-hydroxypropyl and the like.

From all of the above, it is clear to the skilled person that any group whose name is a composite name such as, for instance, arylamino, has to be intended as conventionally construed by the parts from which it derives, e.g. by an amino group which is further substituted by aryl, wherein aryl is as above defined.

Likewise, any of the terms such as, for instance, aryloxy, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, C$_3$-C$_7$ cycloalkyl and heterocyclyl moieties are as above defined.

When R$_3$ stands for a dioxolyl, dioxinyl or dioxepinyl ring, fused with the phenyl ring, that means that compounds of formula (I) are intended as depicted here below:

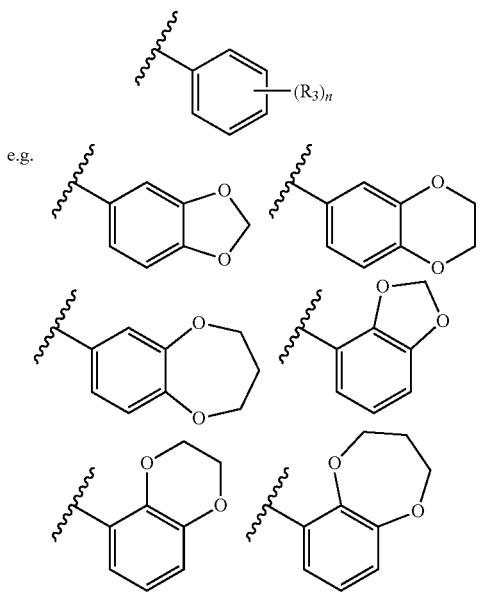

e.g.

According to the present invention and unless otherwise provided, any of the above, R-R$_4$ groups may be optionally substituted, in any of their free positions, by one or more groups, for instance 1 to 6 groups, independently selected from: halogen, nitro, oxo groups (=O), cyano, C$_1$-C$_6$ alkyl, polyfluorinated alkyl, polyfluorinated alkoxy, C$_2$-C$_6$ alkenyl, C$_2$-C$_6$ alkynyl, hydroxyalkyl, aryl, arylalkyl, heteroaryl, heteroarylalkyl, heterocyclyl, heterocyclylalkyl, C$_3$-C$_7$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclylalkyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl alkoxyimino, alkylsulphonylamino, arylsulphonylamino, heterocyclylsulphonylamino, formyl, alkylcarbonyl, arylcarbonyl, cycloalkylcarbonyl, heterocyclylcarbonyl, alkylsulphonyl, arylsulphonyl, aminosulphonyl, alkylaminosulphonyl, dialkylaminosulphonyl, arylaminosulphonyl, heterocyclylaminosulphonyl, arylthio, alkylthio, phosphonate and alkylphosphonate. In their turn, whenever appropriate, each of the above substituent may be further substituted by one or more of the aforementioned groups.

Preferably, the present invention provides compounds of formula (I) as defined above, characterized in that R and R$_1$ are independently hydrogen or an optionally substituted linear or branched C$_1$-C$_6$ alkyl, or, taken together with the nitrogen atom to which they are bonded, form an optionally substituted heterocycle;

R$_2$ is hydrogen or an optionally substituted linear or branched C$_1$-C$_6$ alkyl;

R$_3$ is fluorine, chlorine, bromine, cyano, or an optionally substituted group selected from polyfluorinated C$_1$-C$_6$ alkyl, heterocyclyl, aryloxy, C$_1$-C$_6$ alkylsulphonyl, and when R$_4$ is hydrogen, n is a number between 1 and 3;

when R$_4$ is fluorine, n is a number between 0 and 3.

More preferably, the present invention provides compounds of formula (I) as defined above, characterized in that R and R$_1$ are independently hydrogen or an optionally substituted linear or branched C$_1$-C$_6$ alkyl;

R$_3$ is fluorine, chlorine, bromine, cyano, or an optionally substituted group selected from polyfluorinated C$_1$-C$_6$ alkyl, heterocyclyl, C$_1$-C$_6$ alkylsulphonyl, and when R$_4$ is hydrogen, n is a number between 1 and 2;

when R$_4$ is fluorine, n is a number between 0 and 2.

Specifically preferred compounds (cpd.) according to the present invention are listed below:

1. 4-(2-Amino-ethoxy)-3-(4-bromo-phenyl)-7-fluoro-2H-isoquinolin-1-one,
2. 4-(2-Amino-ethoxy)-7-fluoro-3-(3-trifluoromethyl-phenyl)-2H-isoquinolin-1-one,
3. 4-(2-Amino-ethoxy)-7-fluoro-3-(4-morpholin-4-yl-phenyl)-2H-isoquinolin-1-one,
4. 4-(2-Amino-ethoxy)-3-(3-bromo-4-morpholin-4-yl-phenyl)-7-fluoro-2H-isoquinolin-1-one,
5. 4-(2-Amino-ethoxy)-3-(3-bromo-phenyl)-7-fluoro-2H-isoquinolin-1-one,
6. 4-[4-(2-Amino-ethoxy)-7-fluoro-1-oxo-1,2-dihydro-isoquinolin-3-yl]-benzonitrile,
7. 4-(2-Aminoethoxy)-7-fluoro-3-(4-pyrrolidin-1-yl-phenyl)-2H-isoquinolin-1-one,
8. 4-(2-Amino-ethoxy)-3-(4-chloro-phenyl)-7-fluoro-2H-isoquinolin-1-one,
9. 4-(2-Amino-ethoxy)-7-fluoro-3-(4-methanesulfonyl-phenyl)-2H-isoquinolin-1-one, 10. 4-(2-Amino-ethoxy)-7-fluoro-3-(4-fluoro-phenyl)-2H-isoquinolin-1-one,
11. 3-[4-(2-Amino-ethoxy)-7-fluoro-1-oxo-1,2-dihydro-isoquinolin-3-yl]-benzonitrile,
12. 4-(2-Amino-ethoxy)-3-(4-bromo-phenyl)-7,8-difluoro-2H-isoquinolin-1-one,
13. 4-(2-Amino-ethoxy)-3-(4-chloro-3-methyl-phenyl)-7-fluoro-2H-isoquinolin-1-one,
14. 4-(2-Amino-ethoxy)-3-(3,4-dichloro-phenyl)-7-fluoro-2H-isoquinolin-1-one,
15. 4-(2-Amino-ethoxy)-3-(3,4-difluoro-phenyl)-7-fluoro-2H-isoquinolin-1-one,
16. 5-[4-(2-Amino-ethoxy)-7-fluoro-1-oxo-1,2-dihydro-isoquinolin-3-yl]-2-morpholin-4-yl-benzonitrile,
17. 5-[4-(2-Amino-ethoxy)-7-fluoro-1-oxo-1,2-dihydro-isoquinolin-3-yl]-2-pyrrolidin-1-yl-benzonitrile,
18. 4-(2-Amino-ethoxy)-3-(3-bromo-4-pyrrolidin-1-yl-phenyl)-7-fluoro-2H-isoquinolin-1-one,
19. 4-(2-Amino-ethoxy)-3-(2,3-dihydro-benzo[1,4]dioxin-6-yl)-7-fluoro-2H-isoquinolin-1-one,
20. 4-(2-Amino-ethoxy)-3-benzo[1,3]dioxol-5-yl-7-fluoro-2H-isoquinolin-1-one,
21. 4-(2-Amino-ethoxy)-7-fluoro-3-(3-fluoro-4-methoxy-phenyl)-2H-isoquinolin-1-one,
22. 4-(2-Amino-ethoxy)-7-fluoro-3-(4-trifluoromethoxy-phenyl)-2H-isoquinolin-1-one and
23. 4-(2-Amino-ethoxy)-3-(3,4-dihydro-2H-benzo[b][1,4]dioxepin-7-yl)-7-fluoro-2H-isoquinolin-1-one.

The present invention also provides processes for the preparation of compounds of formula (I) as defined above.

A compound of formula (I) can be prepared according to the general synthetic processes described hereafter in method A and method B.

Method A

Accordingly, a process of the present invention comprises the following steps:

step 1) protecting a compound of formula (II):

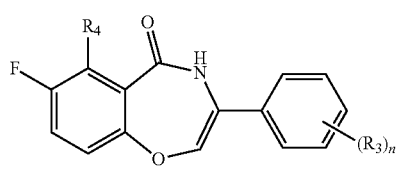

II wherein $R_3$ and $R_4$ are as defined above, with a compound of formula PG-X (III), wherein PG is a suitable protecting group and X is a suitable leaving group;

step 2) rearranging the resultant compound of formula (IV):

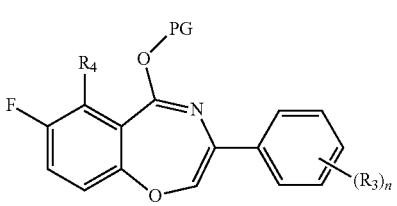

IV wherein $R_3$, $R_4$ and PG are as defined above;

step 3) alkylating the resultant compound of formula (V):

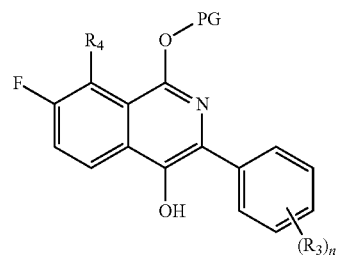

V wherein $R_3$, $R_4$ and PG are as defined above, with a compound of formula (VI):

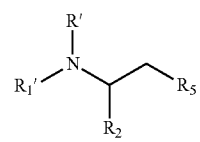

VI wherein $R_2$ is as defined above; R' and $R_1$' have the same meaning of R and $R_1$, respectively, but can also be independently $COOR_6$, wherein $R_6$ is an optionally substituted linear or branched $C_1$-$C_6$ alkyl, like, for instance, tert-butyl, or an optionally substituted linear or branched aryl-$C_1$-$C_6$-alkyl, like, for instance, benzyl; $R_5$ represents a suitable group, such as halogen, like bromine, chlorine or iodine, p-toluenesulphonate, methanesulphonate, trifluoromethanesulphonate or hydroxyl group;

step 4) deprotecting the resultant compound of formula (VII):

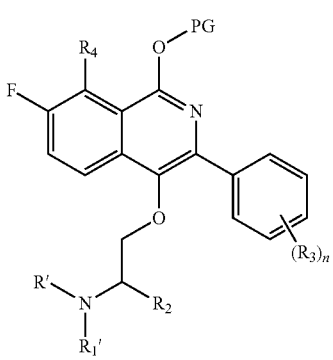

VII wherein R', $R_1$', $R_2$, $R_3$, $R_4$ and PG are as defined above, so as to obtain a compound of formula (I), as defined above, optionally converting a compound of formula (I) into a different compound of formula (I) by known chemical reactions; and/or converting a compound of formula (I) into a pharmaceutically acceptable salt thereof or converting a salt into a free compound of formula (I).

Scheme 1 below illustrates the step sequence of the process according to the present invention with Method A

SCHEME 1

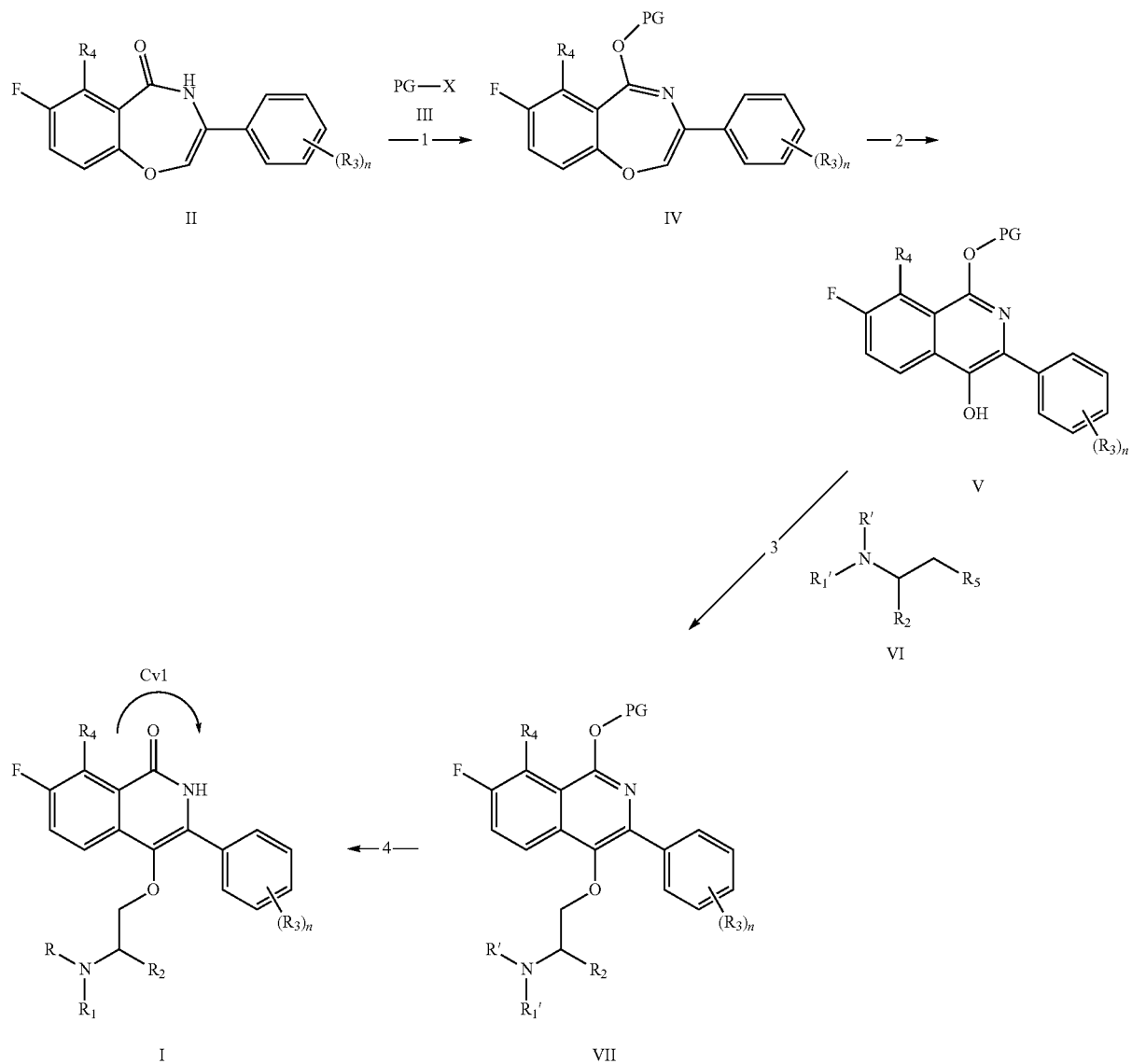

According to step 1 of the process, a compound of formula (II), as defined above, is reacted with a compound of formula (III), wherein PG is a protective group such as methyl, 1-phenylethyl, p-methoxybenzyl, benzyl, and the like, in the presence of a base, such as silver carbonate, and the like, in a suitable solvent, such as toluene, benzene, N,N-dimethylformamide (DMF), N,N-dimethylacetamide (DMA), acetonitrile (ACN), ethyl acetate (EtOAc), tetrahydrofuran (THF), dioxane, and the like, at a temperature ranging from 0° C. to reflux so as to obtain a compound of formula (IV), as defined above.

According to step 2 of the process, a compound of formula (IV), as defined above, is heated, either conventionally or under microwave irradiation, in a solvent such as isopropanol, ethanol, methanol, and the like, so as to afford a compound of formula (V), as defined above. The rearrangement can be carried out as described in Schenker, K. Helv. Chim. Acta 1968, 51, 413-21; or in Wang, S. et al., J. Bioorg. Med. Chem. Lett. 2002, 12, 2367-2370.

According to step 3 of the process, a compound of formula (V), as defined above, is reacted with a compound of formula (VI), as defined above, in the presence of a suitable base, such as sodium, potassium or cesium carbonate, sodium or potassium hydrogencarbonate, triethylamine, diisopropylethylamine, pyridine, sodium or potassium hydride and the like, in a suitable solvent, such as DMF, DMA, ACN, acetone, methanol, ethanol, THF, dioxane, dichloromethane (DCM) and the like, at a temperature ranging from 0° C. to reflux to give a compound of formula (VII), as defined above. When $R_5$ is bromine the reaction is preferentially carried out at room temperature (RT) in DMA as the solvent, using cesium carbonate as the base. When $R_5$ is hydroxyl the reaction is preferentially carried out in the presence of a suitable reagent such as, for instance, diethylazodicarboxylate (DEAD), diisopropylazodicarboxylate (DIAD), ditertbutylazodicarboxylate (DBAD), 1,1'-(azodicarbonyl)dipiperidine (ADDP), and a reagent such as, for instance, trimethylphosphine, tritertbutylphosphine, triphenylphosphine, and the like, in a suitable solvent, such as THF, DMF, DCM, toluene, benzene, and the like, at a temperature ranging from 0° C. to RT.

According to step 4 of the process, final deprotection of a compound of formula (VII), as defined above, to give a compound of formula (I), as defined above, can be performed in one or two steps, depending on the nature of PG, R' and $R_1$' groups.

For example, when PG is benzyl, p-methoxybenzyl or methyl group, and at least one of R' and $R_1$' groups of a compound of formula (VII) is an acid labile nitrogen protective group, such as tertbutoxycarbonyl group and the like, deprotection of the lactam and of the amino group is performed simultaneously and a compound of formula (I) as defined above can be obtained by removing these protective groups under acidic conditions, preferably in the presence of an inorganic or organic acid such as TFA, hydrochloric or methanesulphonic acid, boron tribromide or aluminium trichloride in a suitable solvent such as DCM, dichloroethane, dioxane, a lower alcohol, such as methanol or ethanol, at a temperature ranging from RT to reflux.

Alternatively, when PG is benzyl group and at least one of R' and $R_1$' groups of a compound of formula (VII) is a nitrogen protective group such as benzyloxycarbonyl and the like, deprotection of the lactam and of the amino group is performed simultaneously and a compound of formula (I) as defined above can be obtained by removing these protective groups under reducing conditions, such as, for instance, in the presence of hydrogen or of a hydrogen source, such as, for instance, formic acid, ammonium formate, cyclohexene, 1,4-cyclohexadiene and 1,3-cyclohexadiene, and a hydrogenation catalyst in a suitable solvent, such as ethanol, methanol, EtOAc, or a mixture thereof, and where the catalyst is usually a metal, most often a palladium derivative such as, for instance, palladium on carbon, palladium hydroxide or palladium black.

Alternatively, when PG is benzyl group and at least one of R' and $R_1$' groups of a compound of formula (VII) is a nitrogen protective group such as methoxycarbonyl, ethoxycarbonyl, 9-fluorenylmethoxycarbonyl and the like, a compound of formula (I) as defined above can be obtained by first removing these protective groups under basic conditions, such as, for instance, sodium, potassium or cesium carbonate, sodium, potassium or barium hydroxide, hydrazine, piperidine, morpholine and the like, in a suitable solvent such as methanol, ethanol, water, DMF, DMA and the like, at a temperature ranging from RT to reflux, and then removing the benzyl group (PG) under acidic or reducing conditions, as described above, or viceversa.

Method B

Accordingly, a process of the present invention comprises the following steps:

step 3') alkylating a compound of formula (V'),

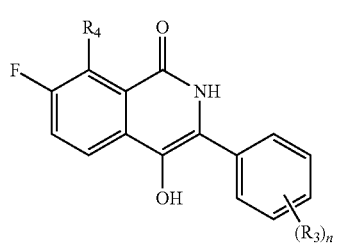

wherein $R_3$ and $R_4$ are as defined above, with a compound of formula (VIa):

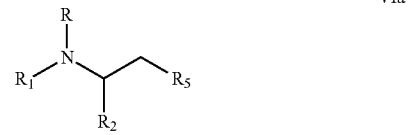

wherein R, $R_1$, $R_2$ and $R_5$ are as defined above, so as to obtain a compound of formula (I), as defined above; or step 3") alkylating a compound of formula (V'), as defined above, with a compound of formula (VIb),

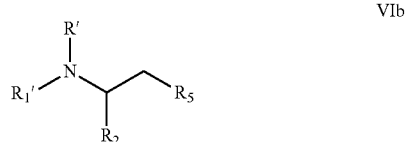

wherein $R_2$ and $R_5$ are as defined above and one or both of R' and $R_1$' is $COOR_6$, wherein $R_6$ is as defined above;

step 4') deprotecting the resultant compound of formula (VIII):

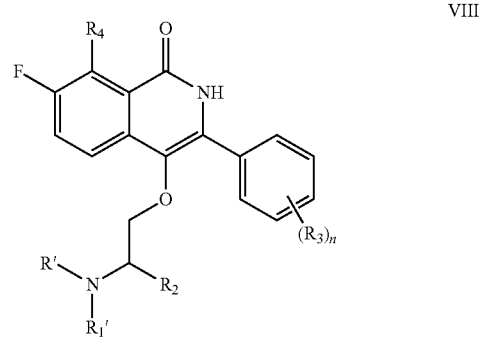

wherein $R_2$, $R_3$ and $R_4$ are as defined above and one or both of R' and $R_1$' is $COOR_6$, wherein $R_6$ is as defined above, so as to obtain a compound of formula (I), as defined above, optionally converting a compound of formula (I) into a different compound of formula (I) by known chemical reactions; and/or converting a compound of formula (I) into a pharmaceutically acceptable salt thereof or converting a salt into a free compound of formula (I).

Scheme 2 below illustrates the step sequence of the process according to the present invention with Method B.

SCHEME 2

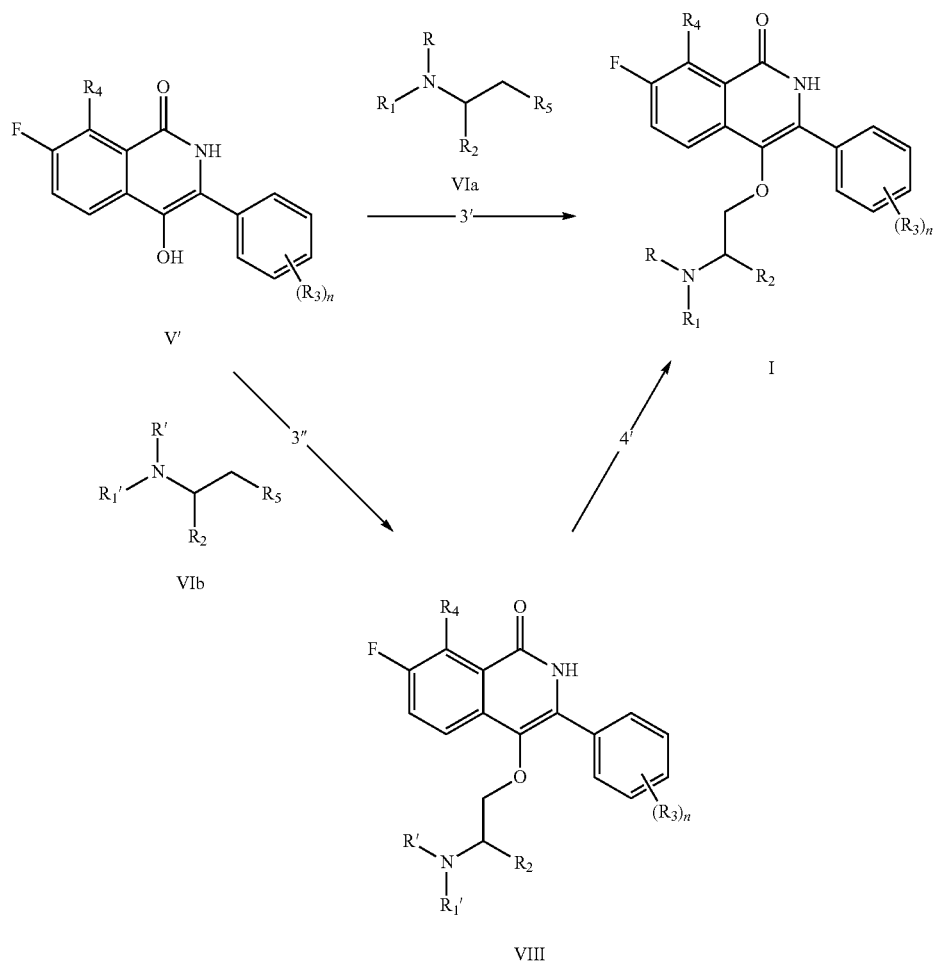

According to step 3' of the process and in analogy with step 3 of Method A, a compound of formula (V'), as defined above, is reacted with a compound of formula (VIa), as defined above, in the presence of a suitable base, such as sodium, potassium or cesium carbonate, sodium or potassium hydrogencarbonate, triethylamine, diisopropylethylamine, pyridine, sodium or potassium hydride and the like, in a suitable solvent, such as DMF, DMA, ACN, acetone, methanol, ethanol, THF, dioxane, dichloromethane (DCM) and the like, at a temperature ranging from 0° C. to reflux to give a compound of formula (I), as defined above. When $R_5$ is bromine the reaction is preferentially carried out at room temperature (RT) in DMA as the solvent, using cesium carbonate as the base. When $R_5$ is hydroxyl the reaction is preferentially carried out in the presence of a suitable reagent such as, for instance, diethylazodicarboxylate (DEAD), diisopropylazodicarboxylate (DIAD), ditertbutylazodicarboxylate (DBAD), 1,1'-(azodicarbonyl)dipiperidine (ADDP), and a reagent such as, for instance, trimethylphosphine, tritertbutylphosphine, triphenylphosphine, and the like, in a suitable solvent, such as THF, DMF, DCM, toluene, benzene, and the like, at a temperature ranging from 0° C. to RT.

According to step 3" of the process and in analogy with step 3', a compound of formula (V'), as defined above, is reacted with a compound of formula (VIb), carrying at least one $COOR_6$ nitrogen protective group, in the same conditions described above.

According to step 4' of the process, final deprotection of a compound of formula (VIII), as defined above, to give a compound of formula (I), as defined above, is performed according to the nature of $R_6$ group(s).

For example, when $COOR_6$ is an acid labile nitrogen protective group such as, for instance, tertbutoxycarbonyl group, it can be removed preferably in the presence of an inorganic or organic acid such as TFA, hydrochloric or methanesulphonic acid, boron tribromide or aluminium trichloride in a suitable solvent such as DCM, dichloroethane, dioxane, a lower alcohol, such as methanol or ethanol, at a temperature ranging from RT to reflux.

Alternatively, when $COOR_6$ is a base labile nitrogen protective group such as, for instance, 9-fluorenylmethoxycarbonyl group, it can be removed preferably under basic conditions, such as, for instance, sodium, potassium or cesium carbonate, sodium, potassium or barium hydroxide, hydrazine, piperidine, morpholine and the like, in a suitable solvent such as methanol, ethanol, water, DMF, DMA and the like, at a temperature ranging from RT to reflux.

Alternatively, when $COOR_6$ is a nitrogen protective group such as, for instance, benzyloxycarbonyl group, it can be removed groups under reducing conditions, such as, for instance, in the presence of hydrogen or of a hydrogen source, such as, for instance, formic acid, ammonium formate, cyclohexene, 1,4-cyclohexadiene and 1,3-cyclohexadiene, and a hydrogenation catalyst in a suitable solvent, such as ethanol, methanol, EtOAc, or a mixture thereof, at a temperature ranging from RT to reflux, and where the catalyst is usually a metal, most often a palladium derivative such as, for instance, palladium on carbon, palladium hydroxide or palladium black.

If necessary or wanted, the processes comprise converting a compound of formula (II) or formula (IV) or formula (V) or formula (VII) or formula (V') or formula (VIII) into the corresponding compound of formula (II) or formula (IV) or formula (V) or formula (VII) or formula (V') or formula (VIII), respectively, by known chemical reactions.

The known chemical reactions for possible conversions of compounds of formula (I) or formula (II) or formula (IV) or formula (V) or formula (VII) or formula (V') or formula (VIII) into the corresponding compounds of formula (I) or formula (II) or formula (IV) or formula (V) or formula (VII) or formula (V') or formula (VIII), respectively, are, for instance:

Conversion A): Conversion of a compound of formula (I) or formula (II) or formula (IV) or formula (V) or formula (VII) or formula (V') or formula (VIII), as defined above, wherein $R_3$ is halogen, into the corresponding compound of formula (I) or formula (II) or formula (IV) or formula (V) or formula (VII) or formula (V') or formula (VIII), respectively, wherein $R_3$ is cyano.

Conversion B): Conversion of a compound of formula (I) or formula (II) or formula (IV) or formula (V) or formula (VII) or formula (V') or formula (VIII), as defined above, wherein $R_3$ is halogen, into the corresponding compound of formula (I) or formula (II) or formula (IV) or formula (V) or formula (VII) or formula (V') or formula (VIII), respectively, wherein $R_3$ is heterocyclyl.

Conversion C): Conversion of a compound of formula (I) or formula (VII), as defined above, wherein at least one of R and $R_1$ is hydrogen, into the corresponding compound of formula (I) or formula (VII), respectively, wherein R and $R_1$ are as defined above but not both hydrogen atoms.

Conversion D): Conversion of a compound of formula (I), as defined above, wherein $R_3$ is hydrogen, into the corresponding compound of formula (I) wherein $R_3$ is halogen.

All the above processes are analogy processes, which can be carried out according to well known methods and under suitable conditions known in the art as reported, for instance, in: Smith, Michael—March's Advanced Organic Chemistry: reactions mechanisms and structure—6$^{th}$ Edition, Michael B. Smith and Jerry March, John Wiley & Sons Inc., New York (N.Y.), 2007.

According to Conversion A, a compound of formula (I) or formula (II) or formula (IV) or formula (V) or formula (VII) or formula (V') or formula (VIII), as defined above, wherein $R_3$ is halogen, can be converted into the corresponding compound of formula (I) or formula (II) or formula (IV) or formula (V) or formula (VII) or formula (V') or formula (VIII), respectively, wherein $R_3$ is cyano, by treatment with a cyanide source such as, for instance, copper (I) cyanide, zinc cyanide, potassium ferrocyanide and the like, optionally in the presence of a palladium catalyst, such as, for instance, palladium (II) diacetate, tetrakis(triphenylphosphine)palladium(0), tris(dibenzylideneacetone)dipalladium(0) and the like; optionally in the presence of a suitable ligand, such as, for instance, 2-dicyclohexylphosphino-2',4',6'-triisopropylbiphenyl, tri-tert-butylphosphine tetrafluoroborate and the like; optionally in the presence of metal zinc; optionally in the presence of a suitable base, such as, for instance, sodium or cesium carbonate, and the like, in a suitable solvent, such as, for instance, DMF, DMA, ACN, dioxane, N-methylpyrrolidone, and the like, at a temperature ranging from RT to reflux.

According to conversion B, a compound of formula (I) or formula (II) or formula (IV) or formula (V) or formula (VII) or formula (V') or formula (VIII), as defined above, wherein $R_3$ is halogen, preferably bromine, can be converted into a corresponding compound of formula (I) or formula (II) or formula (IV) or formula (V) or formula (VII) or formula (V') or formula (VIII), respectively, wherein $R_3$ is heterocyclyl, by treatment with an heterocycle, such as, for instance, piperidine and pyrrolidine, in the presence of a palladium catalyst, such as for instance, palladium (II) diacetate, tetrakis(triphenylphosphine)palladium(0), tris(dibenzylideneacetone)dipalladium(0) and the like; a suitable base, such as for instance, sodium tert-butoxyde, sodium or cesium carbonate, and the like, and a suitable ligand, such as, for instance, 2-(di-tert-butylphosphino)-biphenyl and the like, in a suitable solvent, such as, for instance, DMF, DMA, ACN, dioxane, N-methylpyrrolidone, toluene and the like, at a temperature ranging from RT to reflux.

According to Conversion C, a compound of formula (I) or formula (VII), as defined above, wherein one or both of R' and R1' groups is hydrogen, can be converted into the corresponding compound of formula (I) or formula (VII), respectively, wherein R and R1 are as defined above but not both hydrogen atoms, by reacting the starting material with the suitable aldehyde or ketone in the presence of a reducing agent, such as sodium triacetoxyborohydride, tetramethylammonium triacetoxyborohydride, sodium cyanoborohydride, sodium borohydride, zinc, optionally in the presence of protic acid, such as TFA, hydrochloric, acetic, formic acid and the like, or in the presence of a Lewis acid, such as zinc chloride, zinc bromide, tin(IV) chloride, titanium(IV) chloride, boron trifluoride and the like, in a suitable solvent, such as methanol, ethanol, DCM, acetic acid, DMF and the like, at a temperature ranging from 0° C. to RT.

According to Conversion D, a compound of formula (I), as defined above, wherein $R_3$ is hydrogen, can be converted into the corresponding compound of formula (I) wherein $R_3$ is halogen, by treatment with an electrophilic halogen source like, for instance, N-bromosuccinimide, N-chlorosuccinimide, N-iodosuccinimide, pyridinium hydrobromide perbromide, bromine, iodine, hydrobromic acid/hydrogen peroxide, in a suitable solvent, such as acetonitrile, N,N-dimethylformamide, dioxane, tetrahydrofuran, dimethylsulfoxide, acetic acid, water at a temperature ranging from about room temperature to reflux and for a period of time varying from about 1 hour to about 96 hours.

From all of the above it is clear to the skilled person that any compound of formula (I) bearing a functional group, which can be further elaborated to another functional group, by working according to methods well known in the art, thus leading to other compounds of formula (I), is intended to be comprised within the scope of the present invention.

According to any variant of the process for preparing the compounds of formula (I), the starting materials and any other reactants are known or easily prepared according to known methods. In particular, compounds of formula (III), (VI), (VIa) and (VIb) are commercially available or can be prepared according to known methods, and compounds of formula (II) and (V') can be prepared according to WO2010133647.

From all of the above, it is clear to the skilled person that when preparing compounds of formula (I) according to any of the aforementioned process variants, optional functional groups within the starting materials or intermediates thereof that could give rise to unwanted side reactions, need to be properly protected according to conventional techniques. Likewise, the conversion of these latter into the unprotected compounds may be carried out according to known procedures described, for instance, in: Greene, Theodora W. and Wuts, Peter G. M.—Protective Groups in Organic Synthesis, Third Edition, John Wiley & Sons Inc., New York (N.Y.), 1999.

As it will be easily appreciated, if compounds of formula (I), prepared according to the process described above, are obtained as a mixture of isomers, their separation using conventional techniques into the single isomers of formula (I) is within the scope of the present invention.

Conventional techniques for racemate resolution include, for instance, partitioned crystallization of diastereoisomeric salt derivatives or preparative chiral HPLC and the like. General methods for separation of compounds containing one or more asymmetric centers are reported, for instance, in: Jacques, Jean; Collet, André; Wilen, Samuel H., Enantiomers, Racemates, and Resolutions, John Wiley & Sons Inc., New York (N.Y.), 1981.

In addition, the compounds of formula (I) of the invention may be also prepared according to combinatorial chemistry techniques widely known in the art, for instance by accomplishing the aforementioned reactions between intermediates in a parallel and/or serial manner and by working under solid-phase-synthesis (SPS) conditions.

Pharmacology

PARP-1 is a DNA damage-induced polymerase that catalyzes the cleavage of NAD+ into nicotinamide and ADP-ribose and then uses the latter to synthesize branched nucleic-acid like polymers [poly(ADP-ribose)]. In vivo, the most abundantly poly (ADP-ribosylated) protein is PARP-1 itself, followed by histones. PARP-1 is responsible for 90% of this DNA damage-induced activity while the remaining 10% is due to PARP-2.

Biochemical Assay

Affinity evaluation of the tested compounds and their selectivity with respect to the different PARP isoforms of interest was assessed in a displacement assay.

The identification of compounds capable of binding several PARP proteins is carried out through a screening method including the steps of a) providing a reaction mixture containing:
   the PARP protein isoform under investigation,
   a compound of formula (IP):

IP

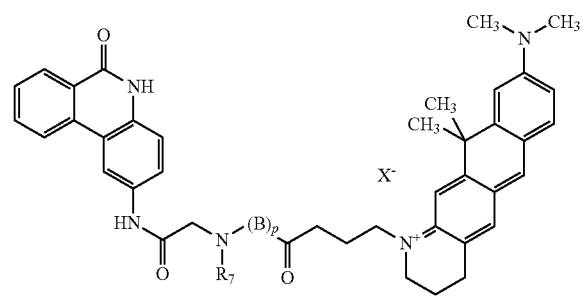

wherein $R_7$ is hydrogen atom or a methyl group, B is $(CH_2)_m$—NH group wherein m is 2 to 6; p is 0 or 1 and $X^-$ is a counterion, and serial dilutions of the test compound;

b) comparing the polarization signal generated in the absence of the test compound with the one generated in the presence of different concentrations of the test compound, and c) evaluating the ability of the test compound to displace the compound of formula (IP) as defined above indicated from a decreased fluorescence polarization level.

Preferably, for the screening method above cited, either the PARP protein and the 5H-phenanthridin-6-one-derived probe of formula (IP) are pre-mixed, or the PARP protein and the test compound are pre-mixed. In a further preferred screening method, the PARP proteins are PARP-1 and PARP-2. The term "PARP protein" encompasses full-length native proteins as well as fragment thereof. More preferably, $R_7$ is hydrogen or methyl, p is 0 or 1; when p is 1, m is 3 or 6, $X^-$ is trifluoroacetate. The 5H-phenanthridin-6-one-derived probe (IP) was selected for its capability of binding to the PARP proteins, both encompassing full-length native proteins and fragment thereof.

The polarization signal can be measured, e.g., by a plate reader such as the Saphire2 (Tecan). The assay was used to test compounds of the present invention. The displacement ability of the test compounds of formula (I) is in correlation with the compounds affinity for the NAD pocket of the enzyme. Specific probes of formula (IP) used in the assay are:

P1.    9-Dimethylamino-11,11-dimethyl-1-(3-{methyl-[(6-oxo-5,6-dihydro-phenanthridin-2-ylcarbamoyl)-methyl]-carbamoyl}-propyl)-2,3,4,11-tetrahydro-naphtho[2,3-g]quinolinium trifluoroacetate;

P2. 9-Dimethylamino-11,11-dimethyl-1-[3-(3-{[(6-oxo-5,6-dihydro-phenanthridin-2-ylcarbamoyl)-methyl]-amino}-propylcarbamoyl)-propyl]-2,3,4,11-tetrahydro-naphtho[2,3-g]quinolinium trifluoroacetate;

P3. 9-Dimethylamino-11,11-dimethyl-1-[3-(6-{[(6-oxo-5,6-dihydro-phenanthridin-2-ylcarbamoyl)-methyl]-amino}-hexylcarbamoyl)-propyl]-2,3,4,11-tetrahydro-naphtho[2,3-g]quinolinium trifluoroacetate.

A compound of formula (IP) as defined above can be prepared as described in WO2010133647.

The assay is based on the use of a probe of formula (IP) that binds to the NAD binding pocket and takes advantage of the significant change in the polarization signal observed upon binding of the probe to PARP-1 and PARP-2. The ability of the probe of formula (IP) to bind full-length PARP-1 and PARP-2 and the assay validation have been previously reported in WO2010133647.

Affinity binding constant (KD) and/or $DC_{50}$s of the test compounds can be determined as explained in WO2010133647.

The assay, by using either probe P1 or probe P3, was used to evaluate the biochemical potency of compounds of formula (I), as reported in Table 1.

TABLE 1

| Compound | PARP-1 ($DC_{50}$ µM) | PARP-1 (Kd µM) * | PARP-2 ($DC_{50}$ µM) | PARP-2 (Kd µM) | PARP-3 ($DC_{50}$ µM) | PARP-3 (Kd µM) |
|---|---|---|---|---|---|---|
| (1) | <0.25† | <0.01† | 1.89 | 1.03 | <0.20† | 0.02 |
| (2) | <0.25 | 0.03 | 2.73 | 1.96 | 0.75 | — |
| (3) | <0.25 | 0.04 | 8.3 | 7.2 | 0.38 | — |
| (4) | <0.25 | <0.01 | 0.53 | 0.24 | 0.32 | 0.09 |
| (5) | <0.25 | 0.01 | 1.59 | 1 | 0.29 | — |
| (6) | <0.25 | 0.01 | 1.06 | 0.54 | 0.36 | — |
| (7) | <0.25 | 0.04 | 1.65 | 1.19 | 0.29 | — |
| (8) | <0.25 | <0.01 | 2.62 | — | 0.22 | 0.03 |
| (10) | <0.25 | 0.03 | 1.93 | — | 0.27 | 0.07 |
| (11) | <0.25 | 0.02 | 1.73 | — | <0.20 | 0.02 |
| (12) | <0.25 | <0.01 | 1.7 | — | <0.20 | 0.02 |

TABLE 1-continued

| Compound | PARP-1 (DC$_{50}$ μM) | PARP-1 (Kd μM) * | PARP-2 (DC$_{50}$ μM) | PARP-2 (Kd μM) | PARP-3 (DC$_{50}$ μM) | PARP-3 (Kd μM) |
|---|---|---|---|---|---|---|
| (13) | <0.25 | <0.01 | 2.31 | — | 0.21 | 0.034 |
| (14) | <0.25 | <0.01 | 1.21 | — | <0.20 | 0.01 |
| (15) | <0.25 | 0.01 | 2.04 | — | <0.20 | 0.02 |
| (18) | <0.25 | 0.06 | 1.78 | — | <0.20 | 0.02 |
| (19) | <0.25 | 0.03 | >10 | — | <0.20 | 0.02 |
| (20) | <0.25 | 0.02 | 3.22 | — | <0.20 | <0.01† |
| (21) | <0.25 | <0.01 | 2.72 | — | 0.25 | 0.05 |

* Assay performed with compound P3 as the probe. In all other cases compound P1 was used as the probe.
† Assay sensitivity limits based on a fitting error <50%.

From the above data, it is clear to a person skilled in the art that compounds of formula (I) of the present invention are highly potent as PARP-1 inhibitors and extremely selective versus PARP-2 (compare PARP-1, PARP-2 and PARP-3 DC$_{50}$ and Kd values in Table 1 above).

Cellular Assays

PAR Assay

Cellular activity of PARP-1 inhibitors was assessed by measuring the inhibition of the hydrogen peroxide induced PAR formation in HeLa cells (ECACC). Cellular PAR levels were measured by immunocytochemistry, and quantified using an ArrayScan vTi instrument (Cellomics Thermo Scientific).

Studies were performed as follows: 6000 cells/well were seeded in 96 well plates (Perkin Elmer) in MEM/10% FCS and incubated for 24 hs at 37° C., 5% carbon dioxide. Test compounds were then added at the required concentration for 30'. DNA damage was then induced adding hydrogen peroxide at the concentration of 0.1 mM for 15 min. Concentration curves were prepared in MEM/10% FCS from compound stocks in dimethylsulfoxide (DMSO), and final DMSO concentration was 0.002% (v/v). Duplicate wells for each concentration point were prepared with a typical highest compound concentration of 20 μM and serial dilution 1:3. Plates were dried and fixed adding a cold methanol-acetone (70:30) solution for 15 min at RT; fixing solution was aspired and wells were air dried for 5 min and then dehydrated in PBS. Non-specific binding sites were blocked by incubating wells for 30 min in PBS containing 5% (w/v) FBS 0.05% Tween20. Wells were then incubated for 1 h at RT in PBS containing anti PAR mouse monoclonal antibody (Anti-PAR, Mouse mAb 10H, Tulip Cat No 1020) diluted 1:200 in blocking solution. After 3 washes in PBS, wells were incubated in PBS (w/v) 5% FBS 0.05% Tween20 containing 2 μg/mL Cy2-conjugated Goat anti mouse secondary antibody (Amersham Pharmacia Biotech cat. No PA 42002) (Absorption maximum 489 nm, fluorescence maximum 506 nm) and 1 μg/mL DAPI (Absorption maximum 359 nm, fluorescence maximum 461 nm) (4',6-diamidino-2-phenylindole dilactate) (Sigma cat. No D9564), a high sensitivity dye for nucleic acid staining. After washing further 3 times in PBS, cellular PAR immunoreactivity was assessed using the ArrayScan vTi instrument, with a Zeiss 10×0.5 N.A. objective, and applying the Cytotoxicity.V3 algorithm (Cellomics/Thermo Fisher) with a XF100 filter. At least 10 fields, corresponding to at least 900 cells, were read for each well. IC$_{50}$ values represent the compound concentration at which cellular PAR signal is diminished by 50% compared with untreated controls.

The following formula is used:

$$IC_{50}=Bottom+(Top-Bottom)/(1+10^{((Log\ EC_{50}-X))});$$

X is the logarithm of concentration. IC$_{50}$ is the response; IC$_{50}$ starts at Bottom and goes to Top with a sigmoid shape.

Given the above assays, compounds of formula (I) of the present invention inhibited PAR formation with IC$_{50}$ values lower than 1 μM, as depicted in table 2, where they are compared with reference compound A, 4-(2-amino-ethoxy)-7-fluoro-3-(4-phenoxy-phenyl)-2H-isoquinolin-1-one, which is described in patent application WO2010133647 and corresponds to the second disclaimed compound of the present patent application.

TABLE 2

| Compound | PAR assay (IC$_{50}$ μM) |
|---|---|
| Ref. compound A | 0.23 |
| (1) | 0.01 |
| (2) | 0.03 |
| (4) | 0.02 |
| (5) | 0.1 |
| (7) | 0.21 |
| (8) | 0.01 |
| (10) | 0.06 |
| (11) | 0.01 |
| (12) | 0.02 |
| (13) | 0.0002 |
| (14) | 0.001 |
| (15) | 0.13 |
| (18) | 0.13 |
| (19) | 0.07 |
| (20) | 0.08 |
| (21) | 0.006 |

Colony Forming Assay

MDA-MB-436 breast cancer BRCA-1 mutated cells were grown at the density of 600 cells/cm$^2$ in RPMI medium supplemented with 10% Fetal Bovine Serum. Twenty-four hours later different doses of compounds were added starting from 10 μM concentration in duplicates. Ten days later, cells were fixed and stained with Crystal Violet. Colonies were counted using Infrared Scanner (Odyssey Li-Cor). Anti proliferative IC$_{50}$ was calculated using Prism.

Pharmacokinetics

The pharmacokinetic profile and the oral bioavailability of the compounds have been investigated in the mouse (Balb, Nu/Nu, Harlan, Italy) in ad hoc pharmacokinetic studies. The compounds were formulated in 10% tween 80/dextrose for intravenous bolus administration while oral administrations were performed using the compounds formulated in 0.5% methylcellulose. A single administration at the dose of 10 mg/kg was given and three male animals for each route were used. All blood samples were taken from retro-orbital vein at 5 min, 30 min, 1 h, 3 h, 6 h, 24 h after intravenous administration and 15 min, 30 min, 1 h, 3 h, 6 h, 24 h after oral administration. Plasma samples were prepared by plasma proteins precipitation adding 200 μL of acetonitrile to 20 μL of plasma in a 96 well plate. After capping and vortex mixing, the plate was centrifuged for 15 min at 4000 rpm. The supernatant was considered as final extract and injected onto the LC-MS-MS system (UPLC system: Waters Acquity using BEH C18 50*2.1 mm 1.7 μm analytical column; MS instrument: Waters TQD equipped with Electro-Spray source operating in positive ion mode). Lower limit of quantification is 5.0 ng/mL, upper limit of quantification is 5000 ng/mL. Non-compartmental method (linear trapezoidal rule and linear regression analysis of natural log-transformed plasma concentrations vs. time data) was used. Absolute bioavailability (F) was calculated from the ratio of average oral to IV (intravenous) dose-normalized plasma AUC (area under curve) values.

The abbreviations used herein have the following meaning:

AUC (area under the plasma concentration vs. time curve up to the last detectable concentration)

Cl (plasma clearance)

Cmax (maximum plasma concentration)

T½(terminal half life)

Vdss (volume of distribution at steady state)

Some representative compounds of formula (I) were evaluated for their pharmacokinetic parameters as reported in Table 3 as mean value.

TABLE 3

| Compound | Cl(IV bolus) mL/min/kg | Vdss (IV bolus) L/Kg | AUC (oral) μM·hours | Cmax (oral) μM | T½ (oral) hours | F on AUC % |
|---|---|---|---|---|---|---|
| (1) | 12 | 3.6 | 27 | 6 | 3.9 | 107 |
| (4) | 44.45 | 7.8 | 5.6 | 3 | 1.43 | 83 |
| (8) | 28.2 | 5.2 | 7.5 | 2.85 | 3 | 74 |
| (12) | 46.3 | 4.5 | 8.15 | 3.15 | 1.77 | 109 |
| (13) | 45 | 5.7 | 10 | 2 | 3 | 128 |
| (14) | 20.5 | 4.2 | 20.3 | 2.8 | 3.5 | 136 |
| (21) | 45.4 | 6.5 | 10.5 | 4.6 | 3.9 | 133 |

From the above, it is clear to the person skilled in the art that compounds of formula (I) possess good to excellent pharmacokinetics profiles and oral bioavailability.

In Vivo Efficacy Studies

CD1, athymic Nu/Nu male mice, from Charles River (Italy), were maintained—in agreement with the European Communities Council Directive no. 86/609/EEC, concerning the protection of animals used for experimental or other scientific purposes—in cages with paper filter cover, food and bedding sterilized and acidified water. Fragments of Capan-1 human pancreatic cancer tumors were implanted subcutaneously. Mice bearing a palpable tumor (100-200 mm$^3$) were selected and randomized into control and treated groups. Each group included seven animals. The treatment started one day after randomization. Compounds of formula (I) were administered by oral route as a methocel suspension. Tumor dimension was measured regularly by calipers during the experiments and tumor mass was calculated as described in Simeoni M. et al., Cancer Res 64, 1094-1101 (2004). The tumor growth inhibition (TGI, %) was calculated according to the equation: % TGI=100−(mean tumor weight of treated group/mean tumor weight of control group)*100.

A representative compound of formula (I), cpd. 1, was evaluated for its anti-tumor activity on Capan-1 BRCA-2 mutated mouse model in combination with temozolomide. Cpd. 1 was administered by oral route at the dose of 100 mg/kg daily for fourteen consecutive days (days 1 to 14). Temozolomide was administered by oral route at the dose of 50 mg/kg on days 3, 4, 5, 6, 7 and 8. Tumor growth and body weight were measured every 3 days. Tumor growth was assessed by caliper. The two diameters were recorded and the tumor weight was calculated according to the following formula: length (mm)×width$^2$/2. The effect of the antitumor treatment was evaluated as the delay in the onset of an exponential growth of the tumor (see for references Anticancer drugs 7:437-60, 1996). This delay (T-C value) was defined as the difference of time (in days) required for the treatment group (T) and the control group (C) tumors to reach a predetermined size (1 g). Toxicity was evaluated on the basis of body weight reduction and animal survival rate. The results are reported in Table 4.

TABLE 4

| Treatment | TGI (%) | BWL (%) | T − C (days) | Toxicity |
|---|---|---|---|---|
| cpd. 1 100 mg/kg* | 21 | 3 | 4 | 0/7 |
| temozolomide 50 mg/kg** | 13 | 2.5 | 1 | 0/7 |
| temozolomide 50 mg/kg + cpd. 1 100 mg/kg*** | 94 | 8 | >40 | 0/7 |

*Oral treatments made on day 1 to 14 daily.
**Treatments made by oral route once a day at days 3, 4, 5, 6, 7 and 8.
***cpd. 1 treatments days 1 to 14, temozolomide treatments, days 3, 4, 5, 6, 7, 8.

The T-C observed when cpd.1 was combined with temozolomide was superior to the expected by the simple addition of T-C obtained by the single treatments indicating strong synergism. From the above, it is clear to the person skilled in the art that compounds of formula (I) possess good synergic tumor growth inhibition activities in combination with cytotoxic agents.

Therefore, the present invention provides compounds of formula (I) useful in therapy.

Compounds of formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of formula (I) may range from about 1 to about 1000 mg per dose, from 1 to 5 times daily. The compounds of the invention can be administered in a variety of dosage forms, e.g., orally, in the form of tablets, capsules, sugar or film coated tablets, liquid solutions or suspensions; rectally in the form of suppositories; parenterally, e.g., intramuscularly, or through intravenous and/or intrathecal and/or intraspinal injection or infusion.

As stated above, the present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose, saccharose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

EXPERIMENTAL SECTION

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods, which are well known in the art.

The short forms and abbreviations used herein have the following meaning:
μM (micromolar)
μL (microliter)
μm (micrometer)
mol (moles)
mM (millimolar)
mmol (millimoles)
nm (nanometers)
g (grams)
mg (milligrams)
ng (nanograms)
$DC_{50}$ (the half maximal Displacement Concentration)
$IC_{50}$ (the half maximal Inhibitory Concentration)
PAR [poly (ADP-ribose)]
MEM (Minimal Essential Medium)
FCS (Fetal Calf Serum)
FBS (Fetal Bovine Serum)
PBS (Phosphate Buffered Saline)
LC-MS (Liquid Chromatography-Mass Spectrometry)
HPLC (High Performance Liquid Chromatography)
TLC (Thin Layer Chromatography)
NMR (Nuclear Magnetic Resonance)
MHz (megahertz)
Hz (Hertz)
J (coupling constant)
ppm (part per million)
δ (chemical shift)
DMSO-$d_6$ (deuterated dimethylsulfoxide)
CDCl$_3$ (deuterated chloroform)
ACN (acetonitrile)
EtOAc (Ethyl acetate)
DCM (dichloromethane)
DMA (N,N-dimethylacetamide)
DMF (N,N-dimethylformamide)
THF (tetrahydrofuran)
TFA (trifluoroacetic acid)
ESI (electrospray ionization)
RT (room temperature)
$R_t$ (retention time)
min (minutes)
h(s) [hour(s)]

With the aim to better illustrate the present invention, without posing any limitation to it, the following examples are now given.

As used herein, the symbols and conventions used in the processes, schemes and examples are consistent with those used in the contemporary scientific literature, for example, the Journal of the American Chemical Society or the Journal of Biological Chemistry.

Unless otherwise noted, all materials were obtained from commercial suppliers, of the best grade and used without further purification. Anhydrous solvent such as DMF, THF, DCM and toluene were obtained from the Aldrich Chemical Company. All reactions involving air- or moisture-sensitive compounds were performed under nitrogen or argon atmosphere.

General Purification and Analytical Methods

Flash Chromatography was performed on silica gel (Merck grade 9395, 60 Å).

When necessary, compounds were purified by preparative HPLC on a Phenomenex Gemini C18 (21×250 mm, 10 μm) column or on a Waters X Terra RP 18 (19×100 mm, 5 μm) column using a Waters FractionLynx System equipped with a 2996 PDA detector and ZQ2000 single quadrupole mass spectrometer, with electrospray ionization (positive and negative mode). Mobile phase A was 0.1% TFA/ACN 95/5, and mobile phase B was ACN. Gradient from 10 to 90% B in 15 min, hold 90% B 3 min. Flow rate 20 mL/min. In alternative, mobile phase A was 0.05% ammonium hydroxide/ACN 95/5 and mobile phase B was ACN. Gradient from 10 to 90% B in 12 min, hold 90% B 2 min. Flow rate 20 mL/min.

HPLC-MS/UV analyses were performed on a LCQ DecaXP (Thermo, San Jose, US) ion trap instrument, equipped with an electrospray ion source. The mass spectrometer is connected to a Surveyor HPLC system (Thermo, San Jose, US) with an UV photodiode array detector (UV detection 215-400 nm). A Phenomenex Gemini C18 column 110 A 50×4.6 mm, 3 μm particle size was used. Mobile phase A was ammonium acetate 5 mM buffer (pH 5.5 with acetic acid)/ACN 95/5, and mobile phase B was ammonium acetate 5 mM buffer (pH 5.5 with acetic acid)/ACN 5/95. Gradient from 0 to 100% B in 7 minutes, hold 100% B 2 minutes. Flow rate 1 mL/min. Injection volume 10 μL. Retention times (HPLC $R_t$) are given in minutes. Mass are given as m/z ratio.

As formerly reported (M. Colombo, F. R. Sirtori, V. Rizzo, Rapid Commun Mass Spectrom 2004, 18(4), 511-517), ESI (+) high-resolution mass spectra (HRMS) were obtained on a Q-Tof Ultima (Waters, Manchester, UK) mass spectrometer directly connected with a Agilent 1100 micro-HPLC system (Palo Alto, US).

$^1$H-NMR spectra were recorded at a constant temperature of 28° C. on a Varian INOVA 400 spectrometer operating at 400.5 MHz and equipped with a 5 mm z-axis PFG Indirect Detection Probe ($^1$H{$^{15}$N-$^{31}$P}).

$^1$H chemical shifts were referenced with respect to the residual solvent signals (DMSO-$d_6$ at 2.50 ppm and CDCl$_3$ at 7.27 ppm). Data are reported as follows: chemical shift (δ), multiplicity (s=singlet, d=doublet, t=triplet, q=quartet, br. s.=broad singlet, td=triplet of doublets, dd=doublet of doublets, ddd=doublet of doublet of doublets, m=multiplet), coupling constants (J, Hz), and number of protons.

Starting Materials for Method A

The following new compounds of formula (II) were obtained as described in WO2010133647, employing suitable starting materials:

3-(4-Bromo-phenyl)-7-fluoro-4H-benzo[f][1,4]oxazepin-5-one

[(II), $R_3$=4-Br, $R_4$=H]
HPLC (254 nm): $R_t$ 6.08 min.

$^1$H NMR (DMSO-d$_6$) δ ppm 6.94 (s, 1 H), 7.20 (dd, J$_{HF}$=9.0, J$_{HH}$=4.6 Hz, 1 H), 7.41-7.45 (m, 3 H), 7.50 (dd, J$_{HF}$=9.0, J$_{HH}$=3.1 Hz, 1 H), 7.57-7.61 (m, 2 H), 9.97 (br. s., 1 H).

HRMS (ESI) calcd for C$_{15}$H$_{10}$BrFNO$_2$ [M+H]$^+$ 333.9874, found 333.9877.

3-(3-Bromo-phenyl)-7-fluoro-4H-benzo[f][1,4]oxazepin-5-one

[(II), R$_3$=3-Br, R$_4$=H]
HPLC (254 nm): R$_t$ 6.06 min.
$^1$H NMR (DMSO-d$_6$) δ ppm 6.98 (s, 1 H), 7.20 (dd, J$_{HF}$=9.0, J$_{HH}$=4.6 Hz, 1 H), 7.34-7.36 (m, 1 H), 7.41-7.46 (m, 1 H), 7.48-7.52 (m, 2 H), 7.56-7.59 (m, 1 H), 7.67 (t, J=1.8 Hz, 1 H), 9.97 (br. s., 1 H).

HRMS (ESI) calcd for C$_{15}$H$_{10}$BrFNO$_2$ [M+H]$^+$ 333.9874, found 333.9876.

4-(7-Fluoro-5-oxo-4,5-dihydro-benzo[f][1,4]oxazepin-3-yl)-benzonitrile

[(II), R$_3$=4-CN, R$_4$=H]
HPLC (254 nm): R$_t$ 5.16 min.
$^1$H NMR (DMSO-d$_6$) δ ppm 7.10 (s, 1 H), 7.23 (dd, J$_{HF}$=9.0, J$_{HH}$=4.6 Hz, 1 H), 7.42-7.47 (m, 1 H), 7.50 (dd, J$_{HF}$=8.8, J$_{HF}$=3.3 Hz, 1 H), 7.68 (d, J=8.6 Hz, 2 H), 7.86 (d, J=8.6 Hz, 2 H), 10.05 (br. s., 1 H).

HRMS (ESI) calcd for C$_{16}$H$_{10}$FN$_2$O$_2$ [M+H]$^+$ 281.0721, found 281.0725.

3-(4-Chloro-phenyl)-7-fluoro-4H-benzo[f][1,4]oxazepin-5-one

[(II), R$_3$=4-Cl, R$_4$=H]
HPLC (254 nm): R$_t$ 6.52 min.
$^1$H NMR (DMSO-d$_6$) δ ppm 6.93 (s, 1 H), 7.20 (dd, J$_{HF}$=9.0, J$_{HH}$=4.6 Hz, 1 H), 7.41-7.44 (m, 1 H), 7.44-7.52 (m, 5 H), 9.97 (br. s., 1 H).

HRMS (ESI) calcd for C$_{15}$H$_{10}$ClFNO$_2$ [M+H]$^+$ 290.0379, found 290.0376.

7-Fluoro-3-(4-methansulfonyl-phenyl)-4H-benzo[f][1,4]oxazepin-5-one

[(II), R$_3$=4-SO$_2$Me, R$_4$=H]
HPLC (254 nm): R$_t$ 4.60 min.
$^1$H NMR (DMSO-d$_6$) δ ppm 3.23 (s, 3 H), 7.08 (s, 1 H), 7.23 (dd, J$_{HF}$=9.0, J$_{HH}$=4.6 Hz, 1 H), 7.41-7.46 (m, 1 H), 7.51 (dd, J$_{HF}$=9.0, J$_{HH}$=3.3 Hz, 1 H), 7.75 (d, J=8.4 Hz, 2 H), 7.93 (d, J=8.4 Hz, 2 H), 10.06 (s, 1 H).

HRMS (ESI) calcd for C$_{16}$H$_{13}$FNO$_4$S [M+H]$^+$ 334.0544, found 334.0546.

7-Fluoro-3-(4-fluoro-phenyl)-4H-benzo[f][1,4]oxazepin-5-one

[(II), R$_3$=4-F, R$_4$=H]
HPLC (254 nm): R$_t$ 6.13 min.
$^1$H NMR (DMSO-d$_6$) δ ppm 6.87 (s, 1 H), 7.20 (dd, J$_{HF}$=8.9, J$_{HH}$=4.5 Hz, 1 H), 7.18-7.26 (m, 2 H), 7.40-7.45 (m, 1 H), 7.48-7.56 (m, 3 H), 9.94 (br. s., 1 H).

HRMS (ESI) calcd for C$_{15}$H$_{10}$F$_2$NO$_2$ [M+H]$^+$ 274.0674, found 274.0681.

7-Fluoro-3-(3-trifluoromethyl-phenyl)-4H-benzo[f][1,4]oxazepin-5-one

[(II), R$_3$=3-CF$_3$, R$_4$=H]
HPLC (254 nm): R$_t$ 6.88 min.
$^1$H NMR (DMSO-d$_6$) δ ppm 7.05 (s, 1 H), 7.20 (dd, J$_{HF}$=9.0, J$_{HH}$=4.4 Hz, 1 H), 7.41-7.46 (m, 1H), 7.51 (dd, J$_{HF}$=9.0, J$_{HH}$=3.3 Hz, 1 H), 7.63 (dd, J=7.7, 6.8 Hz, 1 H), 7.73 (d, J=7.7 Hz, 1 H), 7.80 (d, J=6.8 Hz, 1H), 10.05 (br. s., 1 H).

HRMS (ESI) calcd for C$_{16}$H$_{10}$F$_4$NO$_2$ [M+H]$^+$ 324.0642, found 324.0628.

7-Fluoro-3-(4-morpholin-4-yl-phenyl-4H-benzo[f][1,4]oxazepin-5-one

[(II), R$_3$=4-(morpholin-4-yl), R$_4$=H]
HPLC (254 nm): R$_t$ 5.32 min.
$^1$H NMR (DMSO-d$_6$) δ ppm 3.11-3.15 (m, 4 H), 3.70-3.75 (m, 4 H), 6.77 (s, 1 H), 6.94 (d, J=9.0 Hz, 2 H), 7.18 (dd, J$_{HF}$=9.0, J$_{HH}$=4.6 Hz, 1 H), 7.32 (d, J=9.0 Hz, 2 H), 7.39-7.44 (m, 1 H), 7.49 (dd, J$_{HF}$=9.0, J$_{HH}$=3.3 Hz, 1 H), 9.82 (br. s., 1 H).

HRMS (ESI) calcd for C$_{19}$H$_{18}$FN$_2$O$_3$ [M+H]$^+$ 341.1296, found 341.1294.

3-(3-Bromo-4-morpholin-4-yl-phenyl)-7-fluoro-4H-benzo[f][1,4]oxazepin-5-one

[(II), R$_3$=3-Br-4-(morpholin-4-yl), R$_4$=H]
HPLC (254 nm): R$_t$ 6.03 min.
$^1$H NMR (DMSO-d$_6$) δ ppm 2.95-3.00 (m, 4 H), 3.70-3.77 (m, 4 H), 6.90 (s, 1 H), 7.16 (d, J=8.4 Hz, 1 H), 7.20 (dd, J$_{HF}$=9.0, J$_{HH}$=4.6 Hz, 1 H), 7.39-7.44 (m, 1 H), 7.47 (dd, J=8.4, 2.2 Hz, 1 H), 7.49 (dd, J$_{HF}$=9.0, J$_{HH}$=3.3 Hz, 1 H), 7.68 (d, J=2.2 Hz, 1 H), 9.91 (br. s., 1 H).

HRMS (ESI) calcd for C$_{19}$H$_{17}$BrFN$_2$O$_3$ [M+H]$^+$ 419.0401. found. 419.0401.

3-(4-Bromo-phenyl)-6,7-difluoro-4H-benzo[f][1,4]oxazepin-5-one

[(II), R$_3$=4-Br, R$_4$=F]
HPLC (254 nm): R$_t$ 6.55 min.
$^1$H NMR (DMSO-d$_6$) δ ppm 7.05-7.12 (m, 1 H), 7.07 (s, 1 H), 7.43-7.50 (m, 2 H), 7.57-7.62 (m, 2 H), 7.60-7.67 (m, 1 H), 10.12 (br. s., 1H).

HRMS (ESI) calcd for C$_{15}$H$_9$BrF$_2$NO$_2$ [M+H]$^+$ 351.9779, found 351.9778.

3-(3,4-Dichloro-phenyl)-7-fluoro-4H-benzo[f][1,4]oxazepin-5-one

[(II), R$_3$=3,4-Dichloro, R$_4$=H]
HPLC (254 nm): R$_t$ 6.91 min.
$^1$H NMR (DMSO-d$_6$) δ ppm $^1$H NMR (DMSO-d$_6$) δ ppm 7.03 (s, 1 H), 7.20 (dd, J$_{HF}$=9.0, J$_{HH}$=4.6 Hz, 1 H), 7.41-7.46 (m, 1 H), 7.46-7.52 (m, 2 H), 7.66 (d, J=8.4 Hz, 1 H), 7.75 (d, J=2.2 Hz, 1 H), 9.99 (br. s., 1 H).

HRMS (ESI) calcd for C$_{15}$H$_9$Cl$_2$FNO$_2$ [M+H]$^+$ 323.9989, found 323.9992.

3-(4-Chloro-3-methyl-phenyl)-7-fluoro-4H-benzo[f][1,4]oxazepin-5-one

[(II), R$_3$=4-Chloro-3-methyl, R$_4$=H]
HPLC (254 nm): R$_t$ 6.92 min.
$^1$H NMR (DMSO-d$_6$) δ ppm 2.33 (s, 3 H), 6.91 (s, 1 H), 7.20 (dd, J$_{HF}$=9.0, J$_{HH}$=4.6 Hz, 1 H), 7.32 (dd, J=8.4, 2.0 Hz, 1 H), 7.40-7.45 (m, 2 H), 7.46-7.52 (m, 2 H), 9.93 (br. s., 1 H).

HRMS (ESI) calcd for C$_{16}$H$_{12}$ClFNO$_2$ [M+H]$^+$ 304.0535, found 304.0540.

3-(3,4-Difluoro-phenyl)-7-fluoro-4H-benzo[f][1,4]oxazepin-5-one

[(II), $R_3$=3,4-Difluoro, $R_4$=H]
HPLC (254 nm): $R_t$ 5.47 min.
$^1$H NMR (DMSO-$d_6$) δ ppm 6.95 (s, 1 H), 7.20 (dd, $J_{HF}$=9.0, $J_{HH}$=4.6 Hz, 1 H), 7.32-7.36 (m, 1 H), 7.40-7.45 (m, 1 H), 7.45-7.51 (m, 2 H), 7.57-7.62 (m, 1 H), 9.97 (br. s., 1 H).
HRMS (ESI) calcd for $C_{15}H_9ClF_3NO_2$ [M+H]$^+$ 292.0580, found 292.0586.

3-(3-Bromo-4-pyrrolidin-1-yl-phenyl)-7-fluoro-4H-benzo[f][1,4]oxazepin-5-one

[(II), $R_3$=3-Bromo-4-pyrrolidin-1-yl, $R_4$=H]
HPLC (254 nm): $R_t$ 7.53 min.
$^1$H NMR (DMSO-$d_6$) δ ppm 1.84-1.90 (m, 4 H), 3.30-3.40 (m overlapped by water signal, 4 H), 6.82 (s, 1 H), 6.93 (d, J=8.8 Hz, 1 H), 7.19 (dd, $J_{HF}$=9.0, $J_{HH}$=4.6 Hz, 1 H), 7.31 (dd, J=8.8, 2.2 Hz, 1 H), 7.39-7.44 (m, 1 H), 7.49 (dd, $J_{HF}$=9.0, $J_{HH}$=3.3 Hz, 1 H), 7.55 (d, J=2.2 Hz, 1 H), 9.87 (br. s., 1 H).
HRMS (ESI) calcd for $C_{19}H_{17}BrFN_2O_2$ [M+H]$^+$ 403.0452, found 403.0451.

3-(2,3-Dihydro-benzo[1,4]dioxin-6-yl)-7-fluoro-4H-benzo[f][1,4]oxazepin-5-one

[(II), $R_3$=2,3-Dihydro-[1,4]dioxinyl, $R_4$=H]
HPLC (254 nm): $R_t$ 5.95 min.
$^1$H NMR (DMSO-$d_6$) δ ppm 4.24 (s, 4 H), 6.79 (s, 1 H), 6.86 (d, J=8.4 Hz, 1 H), 6.93 (dd, J=8.4, 2.2 Hz, 1 H), 6.95 (d, J=2.2 Hz, 1 H), 7.19 (dd, $J_{HF}$=9.0, $J_{HH}$=4.6 Hz, 1 H), 7.39-7.44 (m, 1 H), 7.46-7.49 (m, 1 H), 9.83 (br. s., 1 H).
HRMS (ESI) calcd for $C_{17}H_{13}FNO_4$ [M+H]$^+$ 314.0823, found 314.0825.

3-Benzo[1,3]dioxol-5-yl-7-fluoro-4H-benzo[f][1,4]oxazepin-5-one

[(II), $R_3$=[1,3]dioxolyl, $R_4$=H]
HPLC (254 nm): $R_t$ 5.13 min.
$^1$H NMR (DMSO-$d_6$) δ ppm 6.04 (s, 4 H), 6.81 (s, 1 H), 6.92-6.96 (m, 2 H), 7.04 (d, J=1.6 Hz, 1 H), 7.19 (dd, $J_{HF}$=9.0, $J_{HH}$=4.6 Hz, 1 H), 7.40-7.44 (m, 1 H), 7.49 (dd, $J_{HF}$=9.0, $J_{HH}$=3.3 Hz, 1 H, 1 H), 9.86 (br. s., 1 H).
HRMS (ESI) calcd for $C_{16}H_{11}FNO_4$ [M+H]$^+$ 300.0667, found 300.0660.

7-Fluoro-3-(3-fluoro-4-methoxy-phenyl)-4H-benzo[f][1,4]oxazepin-5-one

[(II), $R_3$=3-fluoro-4-methoxy, $R_4$=H]
HPLC (254 nm): $R_t$ 6.08 min.
$^1$H NMR (DMSO-$d_6$) δ ppm 3.85 (s, 3 H), 6.88 (s, 1 H), 7.16-7.22 (m, 2 H), 7.25 (dd, J=8.4, 2.2 Hz, 1 H), 7.35 (dd, $J_{HF}$=12.6, $J_{HH}$=2.2 Hz, 1 H), 7.40-7.44 (m, 1 H), 7.49 (dd, $J_{HF}$=9.0, $J_{HH}$=3.3 Hz, 1 H), 9.91 (br. s., 1H).
HRMS (ESI) calcd for $C_{16}H_{12}F_2NO_3$ [M+H]$^+$ 304.0780, found 304.0781.

EXAMPLE 1

Method A
Step 1

5-Benzyloxy-3-(4-bromo-phenyl)-7-fluoro-benzo[f][1,4]oxazepine

[(IV), $R_3$=4-Br, $R_4$=H, PG=Benzyl]
3-(4-Bromo-phenyl)-7-fluoro-4H-benzo[f][1,4]oxazepin-5-one (7.0 g, 0.021 mol) was dissolved in toluene (100 mL). Benzyl bromide (4.3 g, 0.025 mol) and $Ag_2CO_3$ (8.6 g, 0.031 mol) were added and the reaction mixture was heated at 80° C. until disappearance of the starting material. The solution was filtered through a pad of celite and concentrated to dryness. The crude was purified by flash chromatography on silica gel (n-hexane/EtOAc=7:1) to obtain the title compound (5.3 g, 60% yield) as a thick yellow oil.
HPLC (254 nm): $R_t$ 9.10 min.
$^1$H NMR (DMSO-$d_6$) δ ppm 5.47 (s, 2 H), 7.05 (s, 1 H), 7.20 (dd, $J_{HF}$=9.0, $J_{HH}$=4.6 Hz, 1 H), 7.34-7.39 (m, 1 H), 7.40-7.46 (m, 3 H), 7.50-7.53 (m, 2 H), 7.46-7.53 (m, 3 H), 7.54-7.57 (m, 2 H).
HRMS (ESI) calcd for $C_{22}H_{16}BrFNO_2$ [M+H]$^+$ 424.0343, found 424.0331.

According to this same methodology, but employing suitable starting materials, the following compound was prepared:

5-Benzyloxy-3-(3-bromo-phenyl)-7-fluoro-benzo[f][1,4]oxazepine

[(IV), $R_3$=3-Br, $R_4$=H, PG=Benzyl]
HPLC (254 nm): $R_t$ 9.11 min.
$^1$H NMR (DMSO-$d_6$) δ ppm 5.47 (s, 2 H), 7.08 (s, 1 H), 7.21 (dd, $J_{HF}$=9.0, $J_{HH}$=4.6 Hz, 1 H), 7.24-7.28 (m, 1 H), 7.35-7.38 (m, 1 H), 7.41-7.51 (m, 5 H), 7.55-7.59 (m, 3 H), 7.74 (t, J=1.8 Hz, 1 H).
HRMS (ESI) calcd for $C_{22}H_{16}BrFNO_2$ [M+H]$^+$ 424.0343, found 424.0331.

5-Benzyloxy-3-(3,4-dichloro-phenyl)-7-fluoro-benzo[f][1,4]oxazepine

[(IV), $R_3$=3,4-Dichloro, $R_4$=H, PG=Benzyl]
HPLC (254 nm): $R_t$ 9.14 min.
$^1$H NMR (DMSO-$d_6$) δ ppm 5.48 (s, 2 H), 7.14 (s, 1 H), 7.21 (dd, $J_{HF}$=9.0, $J_{HH}$=4.6 Hz, 1 H), 7.34-7.38 (m, 1 H), 7.40-7.51 (m, 4 H), 7.53-7.58 (m, 3 H), 7.77 (t, J=1.8 Hz, 1 H).
HRMS (ESI) calcd for $C_{22}H_{15}Cl_2FNO_2$ [M+H]$^+$ 414.0459, found 414.0457.

Step 2

1-Benzyloxy-3-(4-bromo-phenyl)-7-fluoro-isoquinolin-4-ol

[(V), $R_3$=4-Br, $R_4$=H, PG=Benzyl]
5-Benzyloxy-3-(4-bromo-phenyl)-7-fluoro-benzo[f][1,4]oxazepine (830 mg, 1.96 mmol) was dissolved in isopropanol, degassed under reduced pressure and purged with argon. The reaction mixture was heated at 140° C. under microwave irradiation for 1 h. The solvent was then evaporated to dryness to afford the title compound as a solid, which was used without any further purification (750 mg, 90% yield).
HPLC (254 nm): $R_t$ 8.75 min.
$^1$H NMR (DMSO-$d_6$) δ ppm 5.59 (s, 2 H), 7.31-7.35 (m, 1 H), 7.39-7.43 (m, 2 H), 7.54-7.59 (m, 2 H), 7.65 (d, J=8.6 Hz, 2 H), 7.72-7.78 (m, 1 H), 7.83 (dd, $J_{HF}$=9.3, $J_{HH}$=2.6 Hz, 1 H), 8.13 (d, J=8.6 Hz, 2 H), 8.32 (dd, $J_{HF}$=9.3, $J_{HH}$=5.3 Hz, 1 H), 9.51 (br. s., 1 H).
HRMS (ESI) calcd for $C_{22}H_{16}BrFNO_2$ [M+H]$^+$ 424.0343 found, 424.0335.

According to this same methodology, but employing suitable starting materials, the following compound was prepared:

1-Benzyloxy-3-(3-bromo-phenyl)-7-fluoro-isoquinolin-4-ol

[(V), $R_3$=3-Br, $R_4$=H, PG=Benzyl]
HPLC (254 nm): $R_t$ 8.40 min.
$^1$H NMR (DMSO-$d_6$) δ ppm 5.59 (s, 2 H), 7.30-7.46 (m, 4 H), 7.52 (d, J=8.0 Hz, 1 H), 7.55-7.59 (m, 2 H), 7.73-7.76 (m, 1 H), 7.85 (dd, $J_{HF}$=9.5, $J_{HF}$=2.4 Hz, 1 H), 8.17 (d, J=7.5 Hz, 1 H), 8.31 (s, 1 H), 8.32 (dd, $J_{HF}$=9.2, $J_{HF}$=5.3 Hz, 1 H), 9.59 (br. s., 1 H).
HRMS (ESI) calcd for $C_{22}H_{16}BrFNO_2$ [M+H]$^+$ 424.0343, found 424.0337.

1-Benzyloxy-3-(3,4-dichloro-phenyl)-7-fluoro-isoquinolin-4-ol

[(V), $R_3$=3,4-Dichloro, $R_4$=H, PG=Benzyl]
HPLC (254 nm): $R_t$ 9.14 min.
$^1$H NMR (DMSO-$d_6$) δ ppm 5.60 (s, 2 H), 7.32-7.35 (m, 1 H), 7.39-7.43 (m, 2 H), 7.54-7.58 (m, 2 H), 7.72 (d, J=8.4 Hz, 1 H), 7.75-7.80 (m, 1 H), 7.86 (dd, $J_{HF}$=9.3, $J_{HF}$=2.6 Hz, 1 H), 8.19 (dd, J=8.4, 2.2 Hz, 1 H), 8.33 (dd, $J_{HF}$=9.2, $J_{HF}$=5.3 Hz, 1 H), 8.37 (d, J=2.2 Hz, 1 H), 9.75 (br. s., 1 H).
HRMS (ESI) calcd for $C_{22}H_{15}Cl_2FNO_2$ [M+H]$^+$ 414.0459, found 414.0447.

Step 3

{2-[1-Benzyloxy-3-(4-bromo-phenyl)-7-fluoro-isoquinolin-4-yloxy-ethyl}-carbamic acid tert-butyl ester

[(VII), R'=$R_2$=$R_4$=H, $R_1$'=tert-butoxycarbonyl, $R_3$=4-Br, PG=Benzyl]
To a solution of 1-benzyloxy-3-(4-bromo-phenyl)-7-fluoro-isoquinolin-4-ol (2.34 g, 5.5 mmol) and commercially available (2-bromo-ethyl)-carbamic acid tert-butyl ester [(VI), R'=$R_2$=H, $R_1$'=tert-butoxycarbonyl] (1.48 g, 6.6 mmol) in DMA (20 mL), $Cs_2CO_3$ (2.34 g, 0.7 mmol) was added and the reaction mixture was left to stir overnight at RT. The solution was then diluted with water and the aqueous phase was extracted with EtOAc. The organic extracts were combined, dried over $Na_2SO_4$, concentrated and the residue was purified by flash chromatography (n-hexane/EtOAc=9:1), thus affording the title compound (1.87 g, 60% yield).
HPLC (254 nm): $R_t$ 9.24 min.
$^1$H NMR (DMSO-$d_6$) δ ppm 1.39 (s, 9 H), 3.27-3.33 (m overlapped by water signal, 2 H), 3.66 (t, J=5.3 Hz, 2 H), 5.63 (s, 2 H), 7.12 (t, J=7.0, 1 H), 7.32-7.37 (m, 1 H), 7.40-7.45 (m, 2 H), 7.56-7.60 (m, 2 H), 7.69 (d, J=8.4 Hz, 2 H), 7.73-7.79 (m, 1 H), 7.88 (dd, $J_{HF}$=9.2, $J_{HF}$=2.6 Hz, 1 H), 8.14 (d, J=8.4 Hz, 2 H), 8.22 (dd, $J_{HF}$=9.0, $J_{HH}$=5.3 Hz, 1H).
HRMS (ESI) calcd for $C_{29}H_{29}BrFN_2O_4$ [M+H]$^+$ 567.1289, found 567.1298.

According to this same methodology, but employing suitable starting materials, the following compounds were prepared:

{2-[1-Benzyloxy-3-(3-bromo-phenyl)-7-fluoro-isoquinolin-4-yloxy]-ethyl}-carbamic acid tert-butyl ester

[(VII), R'=$R_2$=H, $R_1$'=tert-butoxycarbonyl, $R_3$=3-Br, PG=Benzyl]
HPLC (254 nm): $R_t$ 9.71 min.
$^1$H NMR (DMSO-$d_6$) δ ppm 1.38 (s, 9 H), 3.23-3.28 (m, 2 H), 3.67 (t, J=5.5 Hz, 2 H), 5.63 (s, 2 H), 7.04 (t, J=5.1 Hz, 1 H), 7.33-7.37 (m, 1 H), 7.40-7.44 (m, 2 H), 7.46 (dd, J=7.8 Hz, 1 H), 7.56-7.60 (m, 2 H), 7.60 (dd, J=7.8, 1.1 Hz, 1 H), 7.74-7.79 (m, 1 H), 7.90 (dd, $J_{HF}$=9.2, $J_{HH}$=2.4 Hz, 1 H), 8.16 (d, J=7.8 Hz, 1 H), 8.22 (m, 1 H), 8.24 (dd, $J_{HF}$=9.0, $J_{HH}$=5.3 Hz, 1 H).
HRMS (ESI) calcd for $C_{29}H_{29}BrFN_2O_4$ [M+H]$^+$ 567.1289, found 567.1302.

{2-[1-Benzyloxy-3-(3-cyano-phenyl)-7-fluoro-isoquinolin-4-yloxy]-ethyl}-carbamic acid tert-butyl ester

[(VII), R'=$R_2$=H, $R_1$'=tert-butoxycarbonyl, $R_3$=3-CN, PG=Benzyl]
HPLC (254 nm): $R_t$ 7.69 min.
$^1$H NMR (DMSO-$d_6$) δ ppm 1.36 (s, 9 H), 3.22-3.26 (m, 2 H), 3.67 (t, J=5.5 Hz, 2 H), 5.65 (s, 2 H), 7.06 (t, J=5.9 Hz, 1 H), 7.35-7.38 (m, 1 H), 7.40-7.45 (m, 2 H), 7.57-7.62 (m, 2 H), 7.69-7.73 (m, 1 H), 7.76-7.81 (m, 1 H), 7.87-7.94 (m, 2 H), 8.24 (dd, $J_{HF}$=9.2, $J_{HH}$=5.3 Hz, 1 H), 8.42 (t, J=1.5 Hz, 1 H), 8.46 (ddd, J=7.9, 1.6, 1.1 Hz, 1 H).
HRMS (ESI) calcd for $C_{30}H_{29}FN_3O_4$ [M+H]+, 514.2137, found 514.2142.

{2-[1-Benzyloxy-3-(3,4-dichloro-phenyl)-7-fluoro-isoquinolin-4-yloxy]-ethyl}-carbamic acid tert-butyl ester

[(VII), R'=$R_2$=H, $R_1$'=tert-butoxycarbonyl, $R_3$=3,4-Dichloro, PG=Benzyl]
HPLC (254 nm): $R_t$ 9.72 min.
$^1$H NMR (DMSO-$d_6$) δ ppm 1.38 (s, 9 H), 3.26-3.32 (m, 2 H), 3.69 (t, J=5.3 Hz, 2 H), 5.63 (s, 2 H), 7.09 (t, J=5.3 Hz, 1 H), 7.33-7.36 (m, 1 H), 7.40-7.44 (m, 2 H), 7.57-7.60 (m, 2 H), 7.72 (d, J=8.4 Hz, 1 H), 7.75-7.80 (m, 1 H), 7.90 (dd, $J_{HF}$=9.3, $J_{HH}$=2.4 Hz, 1 H), 8.18 (dd, J=8.4, 2.0 Hz, 1 H), 8.24 (dd, $J_{HF}$=9.2, $J_{HH}$=5.3 Hz, 1 H), 8.27(d, J=2.0 Hz, 1 H).
HRMS (ESI) calcd for $C_{29}H_{28}Cl_2FN_2O_4$ [M+H]+, 557.1405, found 557.1420.

Step 4

4-(2-Amino-ethoxy)-3-(4-bromo-phenyl)-7-fluoro-2H-isoquinolin-1-one hydrochloride

[(I), cpd. 1, R=$R_1$=$R_2$=$R_4$=H, $R_3$=4-Br]

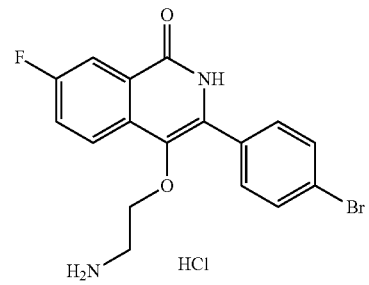 [SMILES: NCCOc1c(-c2ccc(Br)cc2)[nH]c(=O)c2cc(F)ccc12 ; Cl]

{2-[1-Benzyloxy-3-(4-bromo-phenyl)-7-fluoro-isoquinolin-4-yloxy-ethyl}-carbamic acid tert-butyl ester (1.51 g, 2.6 mmol) was treated with trifluoroacetic acid/DCM=1:2 (7.5 mL) and stirred for 2 hs at RT. The reaction mixture was concentrated under reduced pressure. The resulting crude was taken up with diethyl ether, filtered, dissolved in methanol and 4M HCl in dioxane (6 mL) was added. The solution was left to stir for 1 h at RT, concentrated and taken up with diethyl ether, filtered, washed with diethyl ether and dried to give the title compound.

HPLC (254 nm): $R_t$ 3.99 min.

$^1$H NMR (DMSO-$d_6$) δ ppm 2.97-3.04 (m, 2 H), 3.68 (t, J=5.3 Hz, 2 H), 7.64-7.69 (m, 2 H), 7.69-7.72 (m, 2 H), 7.72-7.76 (m, 1 H), 7.92 (dd, $J_{HF}$=9.0, $J_{HH}$=2.7 Hz, 1 H), 7.98 (br., s, 3 H), 8.04 (dd, $J_{HF}$=9.0, $J_{HH}$=5.1 Hz, 1 H), 11.51 (br., s., 1 H).

HRMS (ESI) calcd for $C_{17}H_{15}BrFN_2O_2$ [M+H]$^+$ 377.0296, found 377.0296.

According to this same methodology, but employing suitable starting materials, the following compounds were prepared:

4-(2-Amino-ethoxy)-3-(3-bromo-phenyl)-7-fluoro-2H-isoquinolin-1-one; hydrochloride

[(I), cpd. 5, R=$R_1$=$R_2$=$R_4$=H, $R_3$=3-Br]

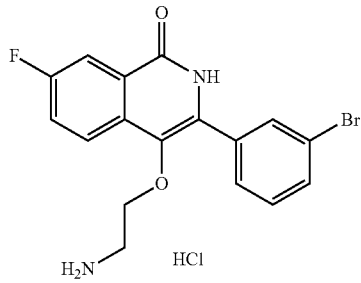 [SMILES: NCCOc1c(-c2cccc(Br)c2)[nH]c(=O)c2cc(F)ccc12 ; Cl]

HPLC (254 nm): $R_t$ 3.99.

$^1$H NMR (DMSO-$d_6$) δ ppm 2.96-3.01 (m, 2 H), 3.70 (t, J=5.1 Hz, 2 H), 7.46-7.50 (m, 1 H), 7.68-7.71 (m, 1 H), 7.72-7.77 (m, 2 H), 7.87 (s, 1 H), 7.92 (dd, $J_{HF}$=9.3, $J_{HH}$=2.6 Hz, 1 H), 8.01 (br., s., 3 H), 8.04 (dd, $J_{HF}$=9.3, $J_{HH}$=5.3 Hz, 1 H), 11.52 (br. s., 1 H).

HRMS (ESI) calcd for $C_{17}H_{15}BrFN_2O_2$ [M+H]$^+$ 377.0296, found 377.0298.

3-[4-(2-Amino-ethoxy)-7-fluoro-1-oxo-1,2-dihydro-isoquinolin-3-yl]-benzonitrile; hydrochloride

[(I), cpd. 11, R=$R_1$=$R_2$=$R_4$=H, $R_3$=3-CN]

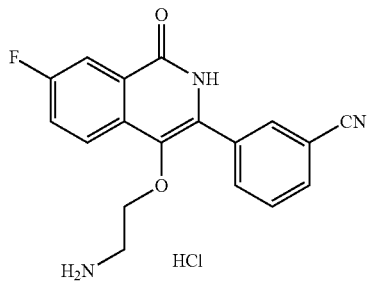 [SMILES: N#Cc1cccc(-c2[nH]c(=O)c3cc(F)ccc3c2OCCN)c1 ; Cl]

HPLC (254 nm): $R_t$ 3.55 min.

$^1$H NMR (DMSO-$d_6$) δ ppm 2.94-3.03 (m, 2 H), 3.68 (t, J=5.2 Hz, 2 H), 7.69-7.74 (m, 1 H), 7.73-7.79 (m, 1 H), 7.91-7.98 (m, 2 H), 7.99 (br. s., 3 H), 8.01-8.06 (m, 1 H), 8.06 (dd, $J_{HF}$=8.9, $J_{HH}$=5.1, 1 H), 8.13 (s, 1 H).

HRMS (ESI) calcd for $C_{18}H_{15}FN_3O_2$ [M+H]$^+$ 324.1143, found 324.1152.

4-(2-Aminoethoxy)-7-fluoro-3-(4-pyrrolidin-1-yl-phenyl)-2H-isoquinolin-1-one; hydrochloride

[(I), cpd. 7, R=$R_1$=$R_2$=$R_4$=H, $R_3$=4-pyrrolidin-1-yl]

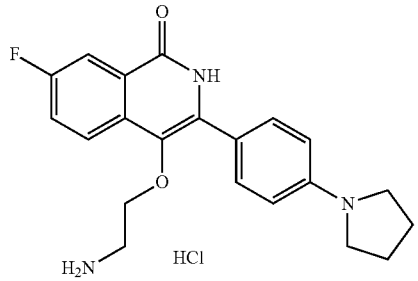 [SMILES: NCCOc1c(-c2ccc(N3CCCC3)cc2)[nH]c(=O)c2cc(F)ccc12 ; Cl]

HPLC (254 nm): $R_t$ 4.48 min.

$^1$H NMR (DMSO-$d_6$) δ ppm 1.95-2.02 (m, 4H), 2.97-3.03 (m, 2 H), 3.28-3.32 (m, 4 H), 3.65 (t, J=5.2 Hz, 2 H), 6.62 (d, J=8.8 Hz, 2 H), 7.57 (d, J=8.8 Hz, 2 H), 7.66-7.70 (m, 1 H), 7.87 (dd, $J_{HF}$=9.3, $J_{HH}$=2.6 Hz, 1 H), 7.99 (dd, $J_{HF}$=9.0, $J_{HH}$=5.1, 1 H), 8.00 (br. s., 3 H), 11.23 (br. s., 1 H).

HRMS (ESI) calcd for $C_{21}H_{23}FN_3O_2$ [M+H]$^+$ 368.1769, found 368.1769.

4-(2-Amino-ethoxy)-3-(3,4-dichloro-phenyl)-7-fluoro-2H-isoquinolin-1-one trifluoroacetate

[(I), cpd. 14, R=$R_1$=$R_2$=$R_4$=H, $R_3$=3,4-Dichloro]

{2-[1-Benzyloxy-3-(3,4-dichloro-phenyl)-7-fluoro-isoquinolin-4-yloxy]-ethyl}-carbamic acid tert-butyl ester (85 mg, 0.15 mmol) was treated with trifluoroacetic acid/DCM=1:10 (4.5 mL) and stirred for 8 hs at RT. The reaction mixture was then concentrated under reduced pressure. The resulting crude was taken up with diethyl ether and filtered, thus affording 55 mg of the title compound (76% yield) as a white solid.

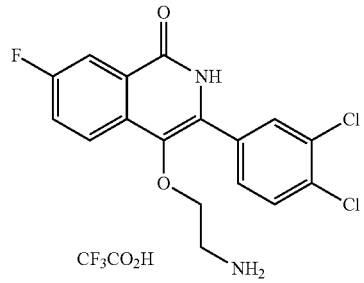 [SMILES: NCCOc1c(-c2ccc(Cl)c(Cl)c2)[nH]c(=O)c2cc(F)ccc12 ; "CF3CO2H"]

HPLC (254 nm): $R_t$ 3.50 min.

$^1$H NMR (DMSO-$d_6$) δ ppm 3.04 (t, J=5.5 Hz, 2 H), 3.69 (t, J=5.5 Hz, 2 H), 7.70-7.77(m, 4 H), 7.90 (br. s., 3 H), 7.93 (dd, $J_{HF}$=8.4, $J_{HH}$=2.7 Hz, 1 H), 8.04 (dd, $J_{HF}$=8.4, $J_{HH}$=5.1 Hz, 1 H), 11.55 (br. s., 1 H).

HRMS (ESI) calcd for $C_{17}H_{14}Cl_2FN_2O_2$ [M+H]$^+$ 367.0411, found 367.0421.

Starting Materials for Method B

The following new compounds of formula (V') were obtained as described in WO2010133647, employing suitable starting materials:

4-(7-Fluoro-4-hydroxy-1-oxo-1,2-dihydro-isoquinolin-3-yl)-benzonitrile

[(V'), $R_3$=4-CN, $R_4$=H]
HPLC (254 nm): $R_t$ 4.88 min.
$^1$H NMR (DMSO-$d_6$) δ ppm 7.70-7.75 (m, 1 H), 7.85-7.88 (m, 3 H), 7.91-7.94 (m, 2 H), 8.05 (dd, $J_{HF}$=9.0, $J_{HH}$=5.3 Hz, 1 H), 8.77 (br. s., 1 H), 11.29 (br. s., 1 H).
HRMS (ESI) calcd for $C_{16}H_{10}FN_2O_2$ [M+H]$^+$ 281.0721, found 281.0729.

3-(4-Chloro-phenyl)-7-fluoro-4-hydroxy-2H-isoquinolin-1-one

[(V'), $R_3$=4-Cl, $R_4$=H]
HPLC (254 nm): $R_t$ 4.38 min.
$^1$H NMR (DMSO-$d_6$) δ ppm 7.50-7.54 (m, 2 H), 7.66-7.72 (m, 3 H), 7.87(dd, $J_{HF}$=9.3, $J_{HH}$=2.7 Hz, 1 H), 8.02 (dd, $J_{HF}$=9.0, $J_{HH}$=5.3 Hz, 1 H), 8.51 (br. s., 1 H), 11.20 (br. s., 1 H).
m/z (ESI) 290 [M+H]+
HRMS (ESI) calcd for $C_{15}H_{10}ClFNO_2$ [M+H]$^+$ 290.0379, found 290.0381.

7-Fluoro-4-hydroxy-3-(4-methansulfonyl-phenyl)-2H-isoquinolin-1-one

[(V'), $R_3$=4-SO$_2$Me, $R_4$=H]
HPLC (254 nm): $R_t$ 3.70 min.
$^1$H NMR (DMSO-$d_6$) δ ppm 3.27 (s, 3 H), 7.70-7.75 (m, 1 H), 7.90 (dd, $J_{HF}$=9.3, $J_{HH}$=2.7 Hz, 1 H), 7.92-7.95 (m, 2 H), 7.99-8.02 (m, 2 H), 8.06 (dd, $J_{HF}$=9.0, $J_{HH}$=5.1 Hz, 1 H), 8.75 (br. s., 1 H), 11.30 (br. s., 1 H).
HRMS (ESI) calcd for $C_{16}H_{13}FNO_4S$ [M+H]$^+$ 334.0544, found 334.0535.

7-Fluoro-3-(4-fluoro-phenyl)-4-hydroxy-2H-isoquinolin-1-one

[(V'), $R_3$=4-F, $R_4$=H]
m/z (ESI) 274 [M+H]+
HRMS (ESI) calcd for $C_{15}H_{10}F_2NO_2$ [M+H]$^+$ 274.0674, found 274.0680.

7-Fluoro-4-hydroxy-3-(3-trifluoromethyl-phenyl)-2H-isoquinolin-1-one

[(V'), $R_3$=3-CF$_3$, $R_4$=H]
HPLC (254 nm): $R_t$ 5.73 min.
$^1$H NMR (DMSO-$d_6$) δ ppm 7.66-7.78 (m, 3 H), 7.89 (dd, $J_{HF}$=9.3, $J_{HH}$=2.7 Hz, 1 H), 7.95-7.99 (m, 1 H), 8.02 (s, 1 H), 8.04 (dd, $J_{HF}$=9.0, $J_{HH}$=5.1 Hz, 1 H), 8.67 (br. s., 1 H), 11.33 (br. s., 1 H).
HRMS (ESI) calcd for $C_{16}H_{10}F_4NO_2$ [M+H]$^+$ 324.0642, found 324.0642.

7-Fluoro-4-hydroxy-3-(4-morpholin-4-yl-phenyl)-2H-isoquinolin-one

[(V'), $R_3$=4-(morpholin-4-yl), $R_4$=H]
HPLC (254 nm): $R_t$ 4.10 min.
$^1$H NMR (DMSO-$d_6$) δ ppm 3.17-3.20 (m, 4 H), 3.74-3.78 (m, 4 H), 7.01 (d, J=9.0 Hz, 2 H), 7.57 (d, J=9.0 Hz, 2 H), 7.63-7.68 (m, 1 H), 7.83 (dd, $J_{HF}$=9.3, $J_{HH}$=2.7 Hz, 1 H), 7.97 (dd, $J_{HF}$=9.0, $J_{HH}$=5.3 Hz, 1 H), 8.22 (br. s., 1 H), 10.99 (br. s., 1 H).
HRMS (ESI) calcd for $C_{19}H_{18}FN_2O_3$ [M+H]$^+$ 341.1296, found 341.1287.

3-(3-Bromo-4-morpholin-4-yl-phenyl)-7-fluoro-4-hydroxy-2H-isoquinolin-1-one

[(V'), $R_3$=3-Br-4-(morpholin-4-yl), $R_4$=H]
HPLC (254 nm): $R_t$ 4.77 min.
$^1$H NMR (DMSO-$d_6$) δ ppm 3.01-3.05 (m, 4 H), 3.76-3.80 (m, 4 H), 7.24 (d, J=8.4 Hz, 1 H), 7.63-7.71 (m, 2 H), 7.86 (dd, $J_{HF}$=9.3, $J_{HH}$=2.7 Hz, 1 H), 7.92 (s, 1 H), 8.01 (dd, $J_{HF}$=9.0, $J_{HH}$=5.3 Hz, 1 H), 8.49 (br. s., 1 H), 11.14 (br. s., 1 H).
HRMS (ESI) calcd for $C_{19}H_{17}BrFN_2O_3$ [M+H]$^+$ 419.0401, found 419.0385.

3-(4-Bromo-phenyl)-7,8-difluoro-4-hydroxy-2H-isoquinolin-one

[(V'), $R_3$=4-Br, $R_4$=F]
HPLC (254 nm): $R_t$ 5.44 min.
$^1$H NMR (DMSO-$d_6$) δ ppm 7.57-7.63 (m, 2 H), 7.63-7.68 (m, 2 H), 7.74-7.80 (m, 1 H), 7.83-7.91 (m, 1 H), 8.52 (br. s., 1 H), 11.15 (br. s., 1 H).
HRMS (ESI) calcd for $C_{15}H_9BrF_2NO_2$ [M+H]$^+$ 351.9779, found 351.9778.

3-(3,4-Dichloro-phenyl)-7-fluoro-4-hydroxy-2H-isoquinolin-one

[(V'), $R_3$=3,4-Dichloro, $R_4$=H]
HPLC (254 nm): $R_t$ 2.32 min.
$^1$H NMR (DMSO-$d_6$) δ ppm 7.64-7.67 (m, 1 H), 7.69-7.63 (m, 1 H), 7.71-7.74 (m, 1 H), 7.88 (dd, $J_{HF}$=9.3, $J_{HH}$=2.7 Hz, 1 H), 7.91 (s, 1 H), 8.04 ($J_{HF}$=9.0, $J_{HH}$=5.3 Hz, 1 H), 8.69 (br. s., 1 H), 11.25 (br.s., 1 H).
HRMS (ESI) calcd for $C_{15}H_9Cl_2FNO_2$ [M+H]$^+$ 323.9989, found 323.9988.

3-(4-Chloro-3-methyl-phenyl)-7-fluoro-4-hydroxy-2H-isoquinolin-1-one

[(V'), $R_3$=4-Chloro-3-methyl, $R_4$=H]
HPLC (254 nm): $R_t$ 5.72 min.
$^1$H NMR (DMSO-$d_6$) δ ppm 2.38 (s, 3 H), 7.47-7.55 (m, 2 H), 7.65 (s, 1 H), 7.67-7.61 (m, 1 H), 7.86 (dd, $J_{HF}$=9.3, $J_{HH}$=2.7 Hz, 1 H), 8.01 ($J_{HF}$=9.0, $J_{HH}$=5.3 Hz, 1 H), 8.49 (br. s., 1 H), 11.13 (br. s., 1 H).
HRMS (ESI) calcd for $C_{16}H_{12}ClFNO_2$ [M+H]$^+$ 304.0535, found 304.0536.

3-(3,4-Difluoro-phenyl)-7-fluoro-4-hydroxy-2H-isoquinolin-1-one

[(V'), $R_3$=3,4-Difluoro, $R_4$=H]
HPLC (254 nm): $R_t$ 4.23 min.
$^1$H NMR (DMSO-$d_6$) δ ppm 7.30-7.34 (m, 1 H), 7.50-7.55 (m, 2 H), 7.68-7.73 (m, 1 H), 7.87 (dd, $J_{HF}$=9.3, $J_{HH}$=2.7 Hz, 1 H), 8.01 ($J_{HF}$=9.0, $J_{HH}$=5.3 Hz, 1 H), 8.60 (br. s., 1 H), 11.21 (br. s., 1 H).
HRMS (ESI) calcd for $C_{15}H_9F_3NO_2$ [M+H]$^+$ 292.0580, found 292.0581.

3-(2,3-Dihydro-benzo[1,4]dioxin-6-yl)-7-fluoro-4-hydroxy-2H-isoquinolin-1-one

[(V'), $R_3=^{2,3}$-Dihydro-[1,4]dioxinyl, $R_4$=H]
HPLC (254 nm): $R_t$ 4.82 min.
$^1$H NMR (DMSO-$d_6$) δ ppm 4.28 (s, 4 H), 6.92 (d, J=8.4 Hz, 1 H), 7.13 (dd, J=8.4, 2.0 Hz, 1 H), 7.19 (d, J=2.0 Hz, 1 H), 7.64-7.69 (m, 1 H), 7.84 (dd, $J_{HF}$=9.3, $J_{HH}$=2.7 Hz, 1 H), 7.98 ($J_{HF}$=9.0, $J_{HH}$=5.3 Hz, 1 H), 8.30 (br. s., 1H), 11.01 (br. s., 1 H).
HRMS (ESI) calcd for $C_{17}H_{13}FNO_4$ [M+H]$^+$ 314.0823, found 314.0825.

3-Benzo[1,3]dioxol-5-yl-7-fluoro-4-hydroxy-2H-isoquinolin-1-one

[(V'), $R_3$=[1,3]dioxolyl, $R_4$=H]
HPLC (254 nm): $R_t$ 4.78 min.
$^1$H NMR (DMSO-$d_6$) δ ppm 6.07 (s, 2 H), 7.00 (d, J=8.2 Hz, 1 H), 7.15 (dd, J=8.2, 1.5 Hz, 1 H), 7.21 (d, J=1.5 Hz, 1 H), 7.64-7.70 (m, 1 H), 7.85 (dd, $J_{HF}$=9.3, $J_{HH}$=2.7 Hz, 1 H), 7.99 ($J_{HF}$=9.0, $J_{HH}$=5.3 Hz, 1 H), 8.33 (br. s., 1H), 11.04 (br. s., 1 H).
HRMS (ESI) calcd for $C_{16}H_{11}FNO_4$ [M+H]$^+$ 300.0667, found 300.0659.

7-Fluoro-3-(3-fluoro-4-methoxy-phenyl)-4-hydroxy-2H-isoquinolin-1-one

[(V'), $R_3$=3-fluoro-4-methoxy, $R_4$=H]
HPLC (254 nm): $R_t$ 4.99 min.
$^1$H NMR (DMSO-$d_6$) δ ppm 3.89 (s, 3 H), 7.25 (dd, $J_{HF}$=9.0, $J_{HH}$=8.4, 1 H), 7.48 (d, J=8.4 Hz, 1 H), 7.54 (dd, $J_{HF}$=12.8, $J_{HH}$=2.0 Hz, 1 H), 7.65-7.71 (m, 1 H), 7.86 (dd, $J_{HF}$=9.3, $J_{HH}$=2.7 Hz, 1 H), 8.01 ($J_{HF}$=9.0, $J_{HH}$=5.1 Hz, 1H), 8.45 (br. s., 1 H), 11.11 (br. s., 1 H).
HRMS (ESI) calcd for $C_{16}H_{12}F_2NO_3$ [M+H]$^+$ 304.0780, found 304.0777.

EXAMPLE 2

Method B
Step 3"

{2-[3-(4-Chloro-phenyl)-7-fluoro-1-oxo-1,2-hihydro-isoquinolin-4-yloxy]-ethyl}-carbamic acid tert-butyl ester

[(VIII), R'=$R_2$=$R_4$=H, $R_1$'=tert-butoxycarbonyl, $R_3$=4-Cl]
To a solution of 3-(4-chloro-phenyl)-7-fluoro-4-hydroxy-2H-isoquinolin-1-one (100 mg, 0.346 mmol) and commercially available (2-bromo-ethyl)-carbamic acid tert-butyl ester [(VIb), R'=$R_2$=H, $R_1$'=tert-butoxycarbonyl) (78 mg, 0.346 mmol) in DMF (2 mL), $Cs_2CO_3$ (135 mg, 0.41 mmol) was added. The reaction mixture was stirred for 4 hs at RT until the starting material was consumed.
The solvent was evaporated to dryness, the residue was diluted with water and the aqueous phase was extracted with DCM. The organic extract was dried over $Na_2SO_4$ and the solvent removed under reduced pressure. The crude was purified by flash chromatography (n-hexane/EtOAc=7:3) to give the title compound (100 mg, 67% yield) as a pale yellow solid.
m/z (ESI) 433 [M+H]+
HRMS (ESI) calcd for $C_{22}H_{23}ClFN_2O_4$ [M+H]$^+$ 433.1325, found 433.1327.

According to this same methodology, but employing suitable starting materials, the following compounds were prepared:

{2-[7-Fluoro-3-(4-methanesulfonyl-phenyl)-1-oxo-1,2-dihydro-isoquinolin-4-yloxy]-ethyl}-carbamic acid tert-butyl ester

[(VIII), R'=$R_2$=$R_4$=H, $R_1$'=tert-butoxycarbonyl, $R_3$=4-$SO_2CH_3$]
m/z (ESI) 494 [M+$NH_4^+$]
HRMS (ESI) calcd for $C_{23}H_{26}FN_2O_6S$ [M+H]$^+$ 477.1490, found 477.1482.

{2-[7-Fluoro-3-(4-fluoro-phenyl)-1-oxo-1,2-dihydro-isoquinolin-4-yloxy]-ethyl}-carbamic acid tert-butyl ester

[(VIII), R'=$R_2$=$R_4$=H, R'=tert-butoxycarbonyl, $R_3$=4-F]
HPLC (254 nm): $R_t$ 6.32 min.
$^1$H NMR (DMSO-$d_6$) δ ppm 1.36 (s, 9 H), 3.04-3.11 (m, 2 H), 3.45 (t, J=5.5 Hz, 2 H), 6.82 (t, J=5.2 Hz, 1 H), 7.27-7.34 (m, 2 H), 7.64-7.70 (m, 1 H), 7.71-7.78 (m, 2 H), 7.89 (dd, $J_{HF}$=9.3, $J_{HH}$=2.7 Hz, 1 H), 7.94 (dd, $J_{HF}$=9.1, $J_{HH}$=5.6 Hz, 1 H), 11.41 (br. s., 1 H).
HRMS (ESI) calcd for $C_{22}H_{23}F_2N_2O_4$ [M+H]$^+$ 439.1440, found 439.1423.

{2-[3-(4-Bromo-phenyl)-7,8-difluoro-1-oxo-1,2-dihydro-isoquinolin-4-yloxy]-ethyl}-carbamic acid tert-butyl ester

[(VIII), R'=$R_2$=H, $R_1$'=tert-butoxycarbonyl, $R_3$=4-Br, $R_4$=F]
HPLC (254 nm): $R_t$ 6.66 min.
$^1$H NMR (DMSO-$d_6$) δ ppm 1.37 (s, 9 H), 3.03-3.14 (m, 2 H), 3.44 (t, J=5.4 Hz, 2 H), 6.87 (t, J=5.2 Hz, 1 H), 7.61-7.72 (m, 5 H), 7.82-7.92 (m, 1 H), 11.37 (br. s., 1 H).
HRMS (ESI) calcd for $C_{22}H_{22}BrF_2N_2O_4$ [M+H]$^+$ 495.0726, found 495.0720.

2-[3-(3,4-Dichloro-phenyl)-7-fluoro-1-oxo-1,2-dihydro-isoquinolin-4-yloxy]-ethyl}-carbamic acid tert-butyl ester

[(VIII), R'=$R_2$=$R_4$=H, $R_1$'=tert-butoxycarbonyl, $R_3$=3,4-Dichloro]
HPLC (254 nm): $R_t$ 3.53 min.
HRMS (ESI) calcd for $C_{22}H_{22}Cl_2FN_2O_4$ [M+H]$^+$ 467.0935, found 467.0934.

{2-[3-(4-Chloro-3-methyl-phenyl)-7-fluoro-1-oxo-1,2-dihydro-isoquinolin-4-yloxy]-ethyl}-carbamic acid tert-butyl ester

[(VIII), R'=$R_2$=$R_4$=H, $R_1$'=tert-butoxycarbonyl, $R_3$=4-Chloro-3-methyl]
HPLC (254 nm): $R_t$ 6.94 min.
$^1$H NMR (DMSO-$d_6$) δ ppm 1.37 (s, 9 H), 2.41 (s, 3 H), 3.08-3.14 (m, 2 H), 3.48 (t, J=5.5 Hz, 2 H), 6.84 (t, J=5.7 Hz, 1 H), 7.50 (d, J=7.5 Hz, 1 H), 7.58 (d, J=7.5 Hz, 1 H), 7.65-7.70 (m, 1 H), 7.70 (br. s., 1 H), 7.89 (dd, $J_{HF}$=9.3, $J_{HH}$=2.7 Hz, 1 H), 7.94 ($J_{HF}$=8.2, $J_{HH}$=5.3 Hz, 1 H), 11.34 (br. s., 1 H).
HRMS (ESI) calcd for $C_{23}H_{25}ClFN_2O_4$ [M+H]$^+$ 447.1482, found 447.1476.

{2-[3-(3,4-Difluoro-phenyl)-7-fluoro-1-oxo-1,2-dihydro-isoquinolin-4-yloxy]-ethyl}-carbamic acid tert-butyl ester

[(VIII), R'=R$_2$=R$_4$=H, R$_1$'=tert-butoxycarbonyl, R$_3$=3,4-Difluoro]

HRMS (ESI) calcd for C$_{22}$H$_{22}$F$_3$N$_2$O$_4$ [M+H]$^+$ 435.1526, found 435.1521.

{2-[3-(2,3-Dihydro-benzo[1,4]dioxin-6-yl)-7-fluoro-1-oxo-1,2-dihydro-isoquinolin-4-yloxy]-ethyl}-carbamic acid tert-butyl ester

[(VIII), R'=R$_2$=R$_4$=H, R'=tert-butoxycarbonyl, R$_3$=2,3-Dihydro-[1,4]dioxinyl]

HRMS (ESI) calcd for C$_{24}$H$_{26}$FN$_2$O$_6$ [M+H]$^+$ 457.1769, found 457.1772.

[2-(3-Benzo[1,3]dioxol-5-yl-7-fluoro-1-oxo-1,2-dihydro-isoquinolin-4-yloxy)-ethyl]-carbamic acid tert-butyl ester

[(VIII), R'=R$_2$=R$_4$=H, R$_1$'=tert-butoxycarbonyl, R$_3$=[1,3]dioxolyl]

HRMS (ESI) calcd for C$_{23}$H$_{24}$FN$_2$O$_6$ [M+H]$^+$ 443.1613, found 443.1616.

{2-[7-Fluoro-3-(3-fluoro-4-methoxy-phenyl)-1-oxo-1,2-dihydro-isoquinolin-4-yloxy]-ethyl}-carbamic acid tert-butyl ester

[(VIII), R'=R$_2$=R$_4$=H, R$_1$'=tert-butoxycarbonyl, R$_3$=3-fluoro-4-methoxy]

HPLC (254 nm): R$_t$ 6.29 min.

$^1$H NMR (DMSO-d$_6$) δ ppm 1.36 (s, 9 H), 3.05-3.12 (m, 2 H), 3.48 (t, J=5.5 Hz, 2 H), 3.91 (s, 3 H), 6.85 (t, J=5.9 Hz, 1 H), 7.27 (dd, J$_{HF}$=8.9 Hz, J$_{HH}$=8.4, 1 H), 7.50 (d, J=8.4 Hz, 1 H), 7.56 (d, J$_{HF}$=11.9 Hz, 1 H), 7.65-7.70 (m, 1 H), 7.89 (dd, J$_{HF}$=9.3, J$_{HH}$=2.7 Hz, 1 H), 7.93 (J$_{HF}$=8.6, J$_{HH}$=5.1 Hz, 1 H), 11.33 (br. s., 1 H).

HRMS (ESI) calcd for C$_{23}$H$_{25}$F$_2$N$_2$O$_5$ [M+H]$^+$ 447.1726, found 447.1713.

Step 3"

{2-[3-(4-Cyano-phenyl)-7-fluoro-1-oxo-1,2-dihydro-isoquinolin-4-yloxy]-ethyl}-carbamic acid tert-butyl ester

[(VIII), R'=R$_2$=R$_4$=H, R$_1$'=tert-butoxycarbonyl, R$_3$=4-CN]

A mixture of Ph$_3$P (422 mg, 1.6 mmol) and (2-hydroxyethyl)-carbamic acid tert-butyl ester (174 mg, 1.08 mmol) was dissolved in anhydrous THF (3 mL) and the resulting solution was cooled to 0° C. The reaction mixture was treated with DEAD (235 mg, 1.35 mmol) and stirred for 10 min. 4-(7-Fluoro-4-hydroxy-1-oxo-1,2-dihydro-isoquinolin-3-yl)-benzonitrile (150 mg, 0.54 mmol) was then added and the reaction mixture was left to stir for 3 hs at RT until disappearance of the starting material. The solvent was removed in vacuo and the crude was purified by flash chromatography (DCM/methanol=95:5) to give the title compound as a white solid.

HPLC (254 nm): R$_t$ 5.66 min.

m/z (ESI) 424 [M+H]+

HRMS (ESI) calcd for C$_{23}$H$_{23}$FN$_3$O$_4$ [M+H]$^+$ 424.1667, found 424.1672.

According to this same methodology, but employing suitable starting materials, the following compounds were prepared:

{2-[7-Fluoro-1-oxo-3-(3-trifluoromethyl-phenyl)-1,2-dihydro-isoquinolin-4-yloxy]-ethyl}-carbamic acid tert-butyl ester

[(VIII), R'=R$_2$=R$_4$=H, R$_1$'=tert-butoxycarbonyl, R$_3$=3-CF$_3$]

HPLC (254 nm): R$_t$ 6.54 min.

m/z (ESI) 467 [M+H]+

HRMS (ESI) calcd for C$_{23}$H$_{23}$F$_4$N$_2$O$_4$ [M+H]$^+$ 467.1589, found 467.1592.

{2-[7-Fluoro-3-(4-morpholin-4-yl-phenyl)-1-oxo-1,2-dihydro-isoquinolin-4-yloxy]-ethyl}-carbamic acid tert-butyl ester

[(VIII), R'=R$_2$=R$_4$=H, R$_1$'=tert-butoxycarbonyl, R$_3$=4-(morpholin-4-yl)]

HPLC (254 nm): R$_t$ 5.74 min.

m/z (ESI) 484 [M+H]$^+$

HRMS (ESI) calcd for C$_{26}$H$_{31}$FN$_3$O$_5$ [M+H]$^+$ 484.2242, found 484.2237.

{2-[3-(3-Bromo-4-morpholin-4-yl-phenyl)-7-fluoro-1-oxo-1,2-dihydro-isoquinolin-4-yloxy]-ethyl}-carbamic acid tert-butyl ester

[(VIII), R'=R$_2$=R$_4$=H, R$_1$'=tert-butoxycarbonyl, R$_3$=3-Br-4-(morpholin-4-yl)]

HPLC (254 nm): R$_t$ 6.42 min.

m/z (ESI) 562 [M+H]+

HRMS (ESI) calcd for C$_{26}$H$_{30}$BrFN$_3$O$_5$ [M+H]$^+$ 562.1347, found 562.1341.

Step 4'

4-[4-(2-Amino-ethoxy)-7-fluoro-1-oxo-1,2-dihydro-isoquinolin-3-yl]-benzonitrile hydrochloride

[(I), cpd. 6, R=R$_1$=R$_2$=R$_4$=H, R$_3$=4-CN]

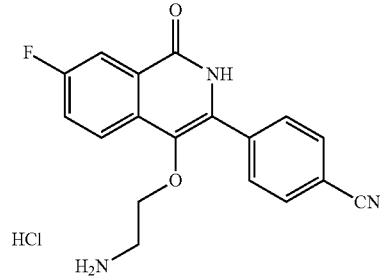 [SMILES: Cl ; N#Cc1ccc(-c2[nH]c(=O)c3cc(F)ccc3c2OCCN)cc1]

{2-[3-(4-Cyano-phenyl)-7-fluoro-1-oxo-1,2-dihydro-isoquinolin-4-yloxy]-ethyl}-carbamic acid tert-butyl ester (40 mg, 0.09 mmol) was dissolved in methanol and treated with 4M HCl (0.6 mL, 2.4 mmol) in dioxane for 5 hs. The solvent was evaporated, the resultant residue was rinsed with methanol and diethyl ether until a precipitate was formed. The solid was filtered and washed with diethyl ether to afford the title compound as a white solid (26 mg, 80% yield).

HPLC (254 nm): R$_t$ 3.52 min.

$^1$H NMR (DMSO-d$_6$) δ ppm 2.97-3.04 (m, 2 H), 3.65 (t, J=5.3 Hz, 2 H), 7.74-7.78 (m, 1 H), 7.88-7.92 (m, 2 H), 7.94

(dd, $J_{HF}$=9.3, $J_{HH}$=2.6 Hz, 1 H), 7.96 (br. s., 3 H), 7.96-8.00 (m, 2 H), 8.07 (dd, $J_{HF}$=9.0, $J_{HH}$=5.3 Hz, 1 H), 11.65 (br. s., 1H).

HRMS (ESI) calcd for $C_{18}H_{15}FN_3O_2$ [M+H]$^+$ 324.1143, found 324.1150.

According to this same methodology, but employing suitable starting materials, the following compounds were prepared:

4-(2-Amino-ethoxy)-3-(4-chloro-phenyl)-7-fluoro-2H-isoquinolin-1-one hydrochloride

[(I), cpd. 8, R=$R_1$=$R_2$=$R_4$=H, $R_3$=4-CN]

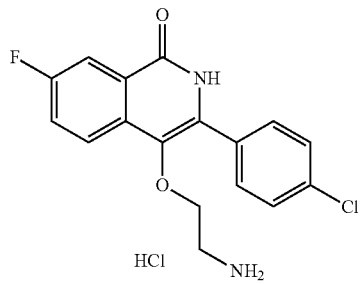 [SMILES: NCCOc1c(-c2ccc(Cl)cc2)[nH]c(=O)c2cc(F)ccc12 ; Cl]

HPLC (254 nm): $R_t$ 3.93.

$^1$H NMR (DMSO-$d_6$) δ ppm 3.00 (t, J=5.2 Hz, 2 H), 3.67 (t, J=5.2 Hz, 2 H), 7.55-7.59 (m, 2 H), 7.70-7.77 (m, 3 H), 7.92 (dd, $J_{HF}$=9.4, $J_{HH}$=2.7 Hz, 1 H), 7.96 (br. s., 3 H), 8.03 (dd, $J_{HF}$=9.1, $J_{HH}$=5.2 Hz, 1 H), 11.51 (br. s., 1 H).

HRMS (ESI) calcd for $C_{17}H_{15}ClFN_2O_2$ [M+H]$^+$ 333.0801, found 333.0797.

4-(2-Amino-ethoxy)-7-fluoro-3-(4-methanesulfonyl-phenyl)-2H-isoquinolin-1-one hydrochloride

[(I), cpd. 9, R=$R_1$=$R_2$=$R_4$=H, $R_3$=4-SO$_2$Me]

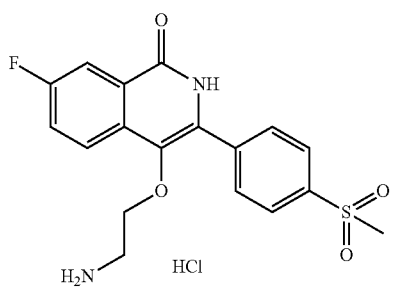 [SMILES: CS(=O)(=O)c1ccc(-c2[nH]c(=O)c3cc(F)ccc3c2OCCN)cc1 ; Cl]

HPLC (254 nm): $R_t$ 3.37 min.

$^1$H NMR (DMSO-$d_6$) δ ppm 3.02 (m, 2 H), 3.31 (s, 3 H), 3.70 (t, J=5.3 Hz, 2 H), 7.74-7.79 (m, 1 H), 7.94 (dd, $J_{HF}$=9.2, $J_{HH}$=2.5 Hz, 1 H), 7.97-8.02 (m, 5 H), 8.03-8.06 (m, 2 H), 8.07 (dd, $J_{HF}$=8.8, $J_{HH}$=5.1 Hz, 1 H), 11.61 (br. s., 1 H).

HRMS (ESI) calcd for $C_{18}H_{18}FN_2O_4S$ [M+H]$^+$ 377.0966, found 377.0963.

4-(2-Amino-ethoxy)-7-fluoro-3-(4-fluoro-phenyl)-2H-isoquinolin-1-one hydrochloride

[(I), cpd. 10, R=$R_1$=$R_2$=$R_4$=H, $R_3$=4-F]

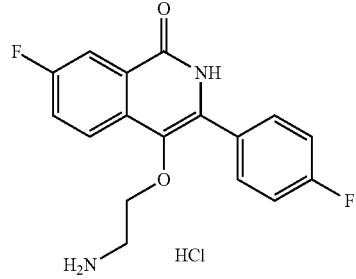 [SMILES: NCCOc1c(-c2ccc(F)cc2)[nH]c(=O)c2cc(F)ccc12 ; Cl]

HPLC (254 nm): $R_t$ 3.64 min.

$^1$H NMR (DMSO-$d_6$) δ ppm 2.94-3.03 (m, 2 H), 3.66 (t, J=5.2 Hz, 2 H), 7.31-7.38 (m, 2 H), 7.70-7.78 (m, 3 H), 7.92 (dd, $J_{HF}$=9.3, $J_{HH}$=2.8 Hz, 1 H), 7.97 (br. s., 3 H), 8.03 (dd, $J_{HF}$=8.8, $J_{HH}$=5.4 Hz, 1 H), 11.49 (br. s., 1 H).

HRMS (ESI) calcd for $C_{17}H_{15}F_2N_2O_2$ [M+H]$^+$ 317.1096, found 317.1101.

4-(2-Amino-ethoxy)-7-fluoro-3-(3-trifluoromethyl-phenyl)-2H-isoquinolin-1-one hydrochloride

[(I), cpd. 2, R=$R_1$=$R_2$=$R_4$=H, $R_3$=3-CF$_3$]

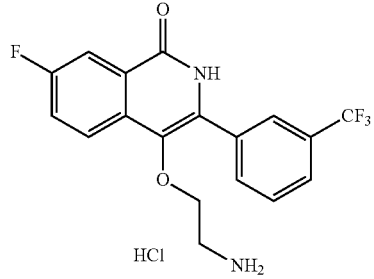 [SMILES: NCCOc1c(-c2cccc(C(F)(F)F)c2)[nH]c(=O)c2cc(F)ccc12 ; Cl]

HPLC (254 nm): $R_t$ 4.25 min.

$^1$H NMR (DMSO-$d_6$) δ ppm 2.90-2.96 (m, 2 H), 3.66 (d, J=5.1 Hz, 2 H), 7.70-7.76 (m, 2 H), 7.83 (d, J=7.7 Hz, 1 H), 7.91 (dd, $J_{HF}$=9.2, $J_{HH}$=2.7 Hz, 1 H), 7.98 (br. s., 3 H), 7.98-8.02 (m, 2 H), 8.04 (dd, $J_{HF}$=8.8, $J_{HH}$=5.5 Hz, 1 H), 11.61 (br. s., 1 H).

HRMS (ESI) calcd for $C_{18}H_{15}F_4N_2O_2$ [M+H]$^+$ 367.1064, found 367.1067.

4-(2-Amino-ethoxy)-7-fluoro-3-(4-morpholin-4-yl-phenyl)-2H-isoquinolin-1-one hydrochloride

[(I), cpd. 3, R=$R_1$=$R_2$=$R_4$=H, $R_3$=4-(morpholin-4-yl)]

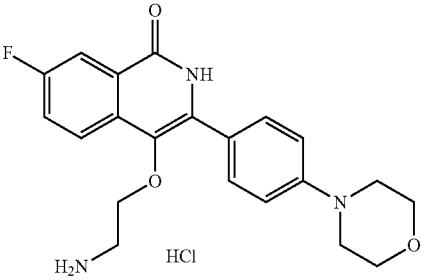 [SMILES: NCCOc1c(-c2ccc(N3CCOCC3)cc2)[nH]c(=O)c2cc(F)ccc12 ; Cl]

HPLC (254 nm): $R_t$ 3.70 min.

$^1$H NMR (DMSO-d$_6$) δ ppm 2.97-3.03 (m, 2 H), 3.21-3.25 (m, 4 H), 3.67 (t, J=5.3 Hz, 2 H), 3.74-3.79 (m, 4 H), 7.04 (d, J=9.0 Hz, 2 H), 7.68-7.72 (m, 1 H), 7.62 (d, J=9.0 Hz, 2 H), 7.88 (dd, J$_{HF}$=9.3, J$_{HH}$=2.7 Hz, 1 H), 8.02 (dd, J$_{HF}$=8.8, J$_{HH}$=5.3 Hz, 1 H), 8.04 (br. s., 3 H), 11.29 (br. s., 1 H).

HRMS (ESI) calcd for C$_{21}$H$_{23}$FN$_3$O$_3$ [M+H]$^+$ 384.1718, found 384.1722.

4-(2-Amino-ethoxy)-3-(3-bromo-4-morpholin-4-yl-phenyl)-7-fluoro-2H-isoquinolin-1-one hydrochloride

[(I), cpd. 4, R=R$_1$=R$_2$=R$_4$=H, R$_3$=3-Br-4-(morpholin-4-yl)]

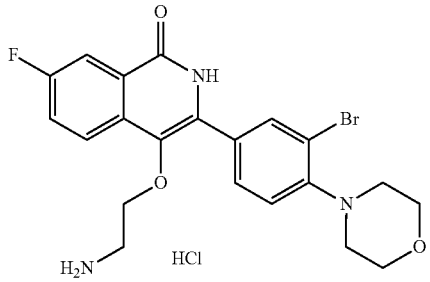 [SMILES: NCCOc1c(-c2ccc(N3CCOCC3)c(Br)c2)[nH]c(=O)c2cc(F)ccc12 ; Cl]

HPLC (254 nm): R$_t$ 4.17 min.

$^1$H NMR (DMSO-d$_6$) δ ppm 2.97-3.04 (m, 2 H), 3.04-3.09 (m, 4 H), 3.70 (t, J=5.3 Hz, 2 H), 3.77-3.81 (m, 4 H), 7.25 (d, J=8.4 Hz, 1 H), 7.71-7.76 (m, 2 H), 7.90 (dd, J$_{HF}$=9.2, J$_{HH}$=2.7 Hz, 1 H), 7.93 (d, J=1.8 Hz, 1 H), 8.03 (br. s., 3 H), 8.04 (dd, J$_{HF}$=9.0, J$_{HH}$=4.8 Hz, 1 H), 11.43 (br. s., 1H).

HRMS (ESI) calcd for C$_{21}$H$_{22}$BrFN$_3$O$_3$ [M+H]$^+$ 462.0823, found 462.0833.

4-(2-Amino-ethoxy)-3-(4-bromo-phenyl)-7,8-difluoro-2H-isoquinolin-1-one hydrochloride

[(I), cpd. 12, R=R$_1$=R$_2$=H, R$_3$=4-Br, R$_4$=F]

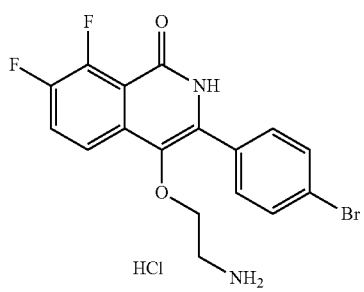 [SMILES: NCCOc1c(-c2ccc(Br)cc2)[nH]c(=O)c2c(F)c(F)ccc12 ; Cl]

HPLC (254 nm): R$_t$ 3.96 min.

$^1$H NMR (DMSO-d$_6$) δ ppm 2.94-3.04 (m, 2 H), 3.64 (t, J=5.4 Hz, 2 H), 7.63-7.68 (m, 2 H), 7.69-7.73 (m, 2 H), 7.76-7.81 (m, 1 H), 7.86-7.95 (m, 1 H), 7.97 (br. s., 3 H), 11.45 (br. s., 1 H).

HRMS (ESI) calcd for C$_{17}$H$_{14}$BrF$_2$N$_2$O$_2$ [M+H]$^+$ 395.0201, found 395.0199.

4-(2-Amino-ethoxy)-3-(3,4-dichloro-phenyl)-7-fluoro-2H-isoquinolin-1-one

[(I), cpd. 14, R=R$_1$=R$_2$=R$_4$=H, R$_3$=3,4-Dichloro]

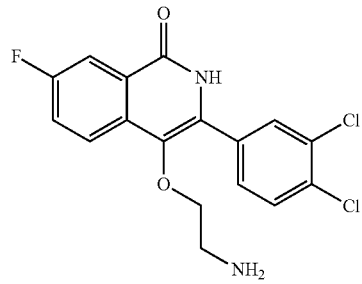 [SMILES: NCCOc1c(-c2ccc(Cl)c(Cl)c2)[nH]c(=O)c2cc(F)ccc12]

The crude hydrochloride, prepared as described above, was purified through preparative HPLC on a Phenomenex Gemini C18 (21×250 mm, 10 μm) column using a Waters Fraction-Lynx System equipped with a 2996 PDA detector and ZQ2000 single quadrupole mass spectrometer, with electrospray ionization (positive and negative mode). Mobile phase A was 0.05% NH$_3$/ACN 95/5, and mobile phase B was ACN. Gradient from 30 to 100% B in 15 min, hold 100% B 3 min. Flow rate 20 mL/min.

HPLC (254 nm): R$_t$ 3.50 min.

$^1$H NMR (DMSO-d$_6$) δ ppm 2.67 (t, J=5.9 Hz, 2 H), 3.49 (t, J=5.9 Hz, 2 H), 7.68-7.71 (m, 1 H), 7.71-7.76 (m, 2 H), 7.89 (dd, J$_{HF}$=9.3, J$_{HH}$=2.7 Hz, 1 H), 7.97 (d, J=1.8 Hz, 1 H), 8.02 (dd, J$_{HF}$=9.0, J$_{HH}$=5.1 Hz, 1 H).

HRMS (ESI) calcd for C$_{17}$H$_{14}$Cl$_2$FN$_2$O$_2$ [M+H]$^+$ 367.0411, found 367.0421.

4-(2-Amino-ethoxy)-3-(4-chloro-3-methyl-phenyl)-7-fluoro-2H-isoquinolin-1-one hydrochloride

[(I), cpd. 13, R=R$_1$=R$_2$=R$_4$=H, R$_3$=4-Chloro-3-methyl]

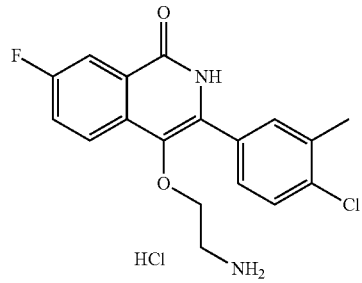 [SMILES: Cc1cc(-c2[nH]c(=O)c3cc(F)ccc3c2OCCN)ccc1Cl ; Cl]

HPLC (254 nm): R$_t$ 4.20 min.

$^1$H NMR (DMSO-d$_6$) δ ppm 2.41 (s, 3 H), 3.01 (t, J=5.5 Hz, 2 H), 3.67 (t, J=5.5 Hz, 2 H), 7.52-7.55 (m, 1 H), 7.56-7.60 (m, 1 H), 7.70 (d, J=1.5 Hz, 1 H), 7.71-7.76 (m, 1 H), 7.90 (dd, J$_{HF}$=9.2, J$_{HH}$=2.7 Hz, 1 H), 7.98 (br. s., 3H), 8.04 (dd, J$_{HF}$=9.0, J$_{HH}$=5.1 Hz, 1 H), 11.45 (br. s., 1 H).

HRMS (ESI) calcd for C$_{18}$H$_{17}$ClFN$_2$O$_2$ [M+H]$^+$ 347.0957, found 347.0964.

4-(2-Amino-ethoxy)-3-(3,4-difluoro-phenyl)-7-fluoro-2H-isoquinolin-1-one hydrochloride

[(I), cpd. 15, R=$R_1$=$R_2$=$R_4$=H, $R_3$=3,4-Difluoro]

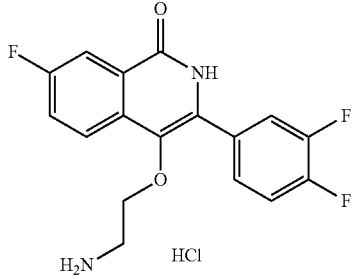 [SMILES: NCCOc1c(-c2ccc(F)c(F)c2)[nH]c(=O)c2cc(F)ccc12 ; Cl]

HPLC (254 nm): $R_t$ 2.85 min.
$^1$H NMR (DMSO-$d_6$) δ ppm 3.02 (t, J=5.3 Hz, 2 H), 3.68 (t, J=5.3 Hz, 2 H), 7.55-7.60 (m, 2 H), 7.72-7.76 (m, 1 H), 7.76-7.80 (m, 1 H), 7.92 (dd, $J_{HF}$=9.2, $J_{HH}$=2.7 Hz, 1 H), 7.98 (br. s., 3 H), 8.05 (dd, $J_{HH}$=9.0, $J_{HF}$=5.1 Hz, 1 H), 11.52 (br. s., 1 H).
HRMS (ESI) calcd for $C_{17}H_{14}F_3N_2O_2$ [M+H]$^+$ 335.1002, found 335.1006.

4-(2-Amino-ethoxy)-3-(2,3-dihydro-benzo[1,4]dioxin-6-yl)-7-fluoro-2H-isoquinolin-1-one

[(I), cpd. 19, R=$R_1$=$R_2$=$R_4$=H, $R_3$=2,3-Dihydro-[1,4]dioxinyl]

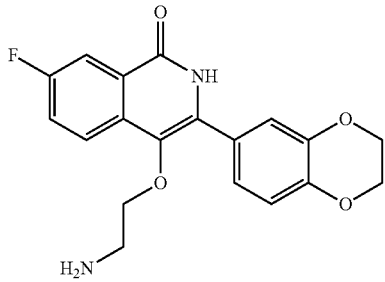 [SMILES: NCCOc1c(-c2ccc3c(c2)OCCO3)[nH]c(=O)c2cc(F)ccc12]

The crude hydrochloride, prepared as described above, was purified through preparative HPLC on a Phenomenex Gemini C18 (21×250 mm, 10 μm) column using a Waters FractionLynx System equipped with a 2996 PDA detector and ZQ2000 single quadrupole mass spectrometer, with electrospray ionization (positive and negative mode). Mobile phase A was 0.05% $NH_3$/ACN 95/5, and mobile phase B was ACN. Gradient from 5 to 95% B in 25 min, hold 95% B 3 min. Flow rate 20 mL/min.

HPLC (254 nm): $R_t$ 3.67 min.
$^1$H NMR (DMSO-$d_6$) δ ppm 2.65(t, J=5.7 Hz, 2 H), 3.47 (t, J=5.7 Hz, 2 H), 4.27-4.32 (m, 4 H), 6.95 (d, J=8.6 Hz, 1 H), 7.18 (dd, J=8.6, 2.0 Hz, 1 H), 7.19 (d, J=2.0 Hz, 1 H), 7.66-7.70 (m, 1 H), 7.88 (dd, $J_{HF}$=9.3, $J_{HH}$=2.7 Hz, 1 H), 7.99 (dd, $J_{HF}$=9.0, $J_{HH}$=5.3 Hz, 1 H).
HRMS (ESI) calcd for $C_{19}H_{18}FN_2O_4$ [M+H]$^+$ 357.1245, found 357.1241.

4-(2-Amino-ethoxy)-3-benzo[1,3]dioxol-5-yl-7-fluoro-2H-isoquinolin-1-one hydrochloride

[(I), cpd. 20, R=$R_1$=$R_2$=$R_4$=H, $R_3$=[1,3]dioxolyl]

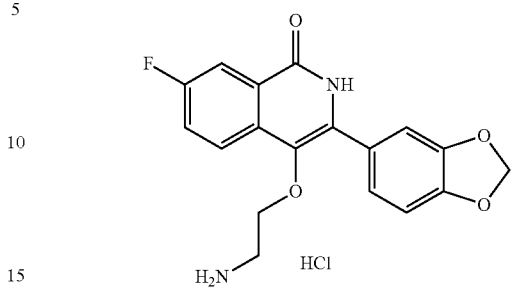

HPLC (254 nm): $R_t$ 2.74 min.
$^1$H NMR (DMSO-$d_6$) δ ppm 2.97-3.04 (m, 2 H), 3.68 (t, J=5.3 Hz, 2 H), 6.11 (s, 2 H), 7.04 (d, J=8.1 Hz, 1 H), 7.21 (dd, J=8.1, 1.5 Hz, 1 H), 7.24 (d, J=1.5 Hz, 1 H), 7.69-7.74 (m, 1 H), 7.89 (dd, $J_{HF}$=9.2, $J_{HH}$=2.7 Hz, 1 H), 8.00 (br. s., 3 H), 8.02 (dd, $J_{HF}$=8.8, $J_{HH}$=5.1 Hz, 1 H).
HRMS (ESI) calcd for $C_{18}H_{16}FN_2O_4$ [M+H]$^+$ 343.1089, found 343.1082.

4-(2-Amino-ethoxy)-7-fluoro-3-(3-fluoro-4-methoxy-phenyl)-2H-isoquinolin-1-one hydrochloride

[(I), cpd. 21, R=$R_1$=$R_2$=$R_4$=H, $R_3$=3-fluoro-4-methoxy]

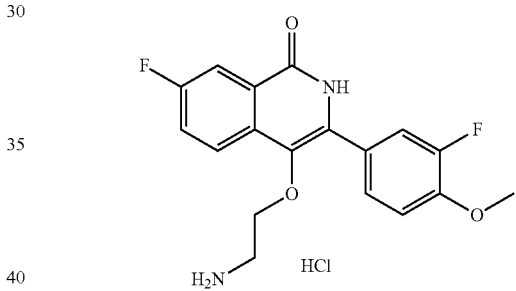

HPLC (254 nm): $R_t$ 3.75 min.
$^1$H NMR (DMSO-$d_6$) δ ppm 2.98-3.04 (m, 2 H), 3.67 (t, J=5.1 Hz, 2 H), 3.92 (s, 3 H), 7.28 (dd, $J_{HF}$=9.0, $J_{HH}$=8.4 Hz, 1 H), 7.52 (d, J=8.4 Hz, 1 H), 7.58 (dd, $J_{HF}$=12.6, $J_{HH}$=2.0 Hz, 1 H), 7.70-7.75 (m, 1 H), 7.91 (dd, $J_{HF}$=9.3, $J_{HH}$=2.7 Hz, 1 H), 8.00 (br. s., 3 H), 8.03 (dd, $J_{HF}$=9.2, $J_{HF}$=4.8 Hz, 1 H), 11.42 (br. s., 1 H).
HRMS (ESI) calcd for $C_{18}H_{17}F_2N_2O_3$ [M+H]$^+$ 347.1202, found 347.1196.

Conversion A

3-(1-Benzyloxy-7-fluoro-4-hydroxy-isoquinolin-3-yl)-benzonitrile

[(V), $R_3$=3-CN, $R_4$=H, PG=Benzyl]

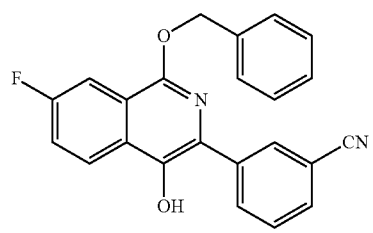 [SMILES: N#Cc1cccc(-c2nc(OCc3ccccc3)c3cc(F)ccc3c2O)c1]

A mixture of 1-benzyloxy-3-(3-bromo-phenyl)-7-fluoro-isoquinolin-4-ol (400 mg, 0.94 mmol), Zn (33 mg, 0.5 mmol), Zn(CN)$_2$ (241 mg, 2 mmol), Pd$_2$(dba)$_3$.CHCl$_3$ (59 mg, 0.056 mmol) and tri-tert-butylphosphine tetrafluoroborate (44 mg, 0.15 mmol) was dissolved in degassed N-methylpyrrolidone (20 mL).

After degassing the mixture under reduced pressure, it was exposed to nitrogen and heated to 90° C. for 2 hs. The reaction mixture was then cooled down, filtered, diluted with water and extracted with EtOAc. The combined organic layers were washed with water, dried over Na$_2$SO$_4$ and evaporated to dryness. The crude was purified by flash chromatography (n-hexane/EtOAc=8:2) to give the title compound as a yellow solid (210 mg, 60% yield).

$^1$H NMR (CDCl$_3$) δ ppm 5.10 (s, 2 H), 7.20-7.46 (m, 9 H), 7.51-7.58 (m, 2 H), 8.13-8.21 (m, 1 H).

HRMS (ESI) calcd for C$_{23}$H$_{16}$FN$_2$O$_2$ [M+H]$^+$ 371.1191, found 371.1193.

Conversion B

{2-[7-Fluoro-1-oxo-3-(4-pyrrolidin-1-yl-phenyl)-1,2-dihydro-isoquinolin-4-yloxy]-ethyl}-carbamic acid tert-butyl ester

[(VII), R'=R$_2$=H, R$_1$'=tert-butoxycarbonyl, R$_3$=4-pyrrolidin-1-yl, R$_4$=H, PG=Benzyl]

A mixture of 2-[1-benzyloxy-3-(4-bromo-phenyl)-7-fluoro-isoquinolin-4-yloxy]-ethyl}-carbamic acid tert-butyl ester (100 mg, 0.176 mmol), sodium tert-butoxyde (26 mg, 0.264 mmol), Pd(OAc)$_2$ (2 mg, 0.007 mmol), 2-(di-tert-butylphosphino)-biphenyl (5 mg, 0.016 mmol) and pyrrolidine (18 mg, 0.25 mmol) was dissolved in toluene (3 mL) The reaction mixture was degassed, purged with argon and heated at 90° C. for 2 hs. The solution was filtered through a pad of Celite, and the solvent was evaporated under reduced pressure. The residue was diluted with EtOAc and the organic phase was washed with brine. The organic extract was dried over Na$_2$SO$_4$ and evaporated to dryness. The crude was purified by flash chromatography on silica gel (n-hexane/EtOAc=85:15) to give the title compound as a white solid.

m/z (ESI) 558 [M+H]+

HRMS (ESI) calcd for C$_{33}$H$_{37}$FN$_3$O$_4$ [M+H]$^+$ 558.2763, found 558.2768.

Conversion D 4-(2-Amino-ethoxy)-3-(3-bromo-4-pyrrolidin-1-yl-phenyl)-7-fluoro-2H-isoquinolin-1-one

[(I), cpd. 18, R=R$_1$=R$_2$=R$_4$=H, R$_3$=3-bromo-4-pyrrolidin-1-yl]

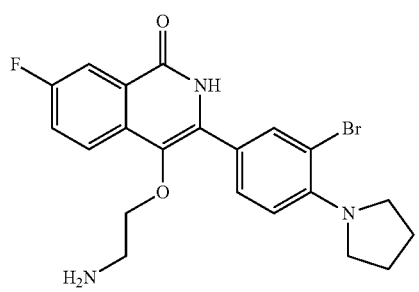 [SMILES: NCCOc1c(-c2ccc(N3CCCC3)c(Br)c2)[nH]c(=O)c2cc(F)ccc12]

To a stirred suspension of 4-(2-aminoethoxy)-7-fluoro-3-(4-pyrrolidin-1-yl-phenyl)-2H-isoquinolin-1-one hydrochloride [(I), cpd. 7, R=R$_1$=R$_2$=H, R$_3$=4-pyrrolidin-1-yl, R$_4$=H] (15 mg, 0.037 mmol) in dry THF (0.3 mL), kept at room temperature, pyridinium hydrobromide perbromide (13 mg, 0.04 mmol) were added. The reaction mixture was stirred for 1 hour, the volatiles were then evaporated in vacuo and the resulting crude was purified through preparative HPLC on a Phenomenex Gemini C18 (21×250 mm, 10 µm) column, using a Waters FractionLynx System equipped with a 2996 PDA detector and ZQ2000 single quadrupole mass spectrometer, with electrospray ionization (positive and negative mode). Mobile phase A was 0.05% NH$_3$/ACN 95/5, and mobile phase B was ACN. Gradient from 5 to 95% B in 25 min, hold 95% B 3 min. Flow rate 20 mL/min.

HPLC (254 nm): R$_t$ 4.76 min.

$^1$H NMR (DMSO-d$_6$) δ ppm 1.88-1.93 (m, 4 H), 2.69 (t, J=5.7 Hz, 2 H), 3.40-3.44 (m, 4 H), 3.48 (t, J=5.7 Hz, 2 H), 7.00 (d, J=8.6 Hz, 1 H), 7.58 (dd, J=8.6, 2.0 Hz, 1 H), 7.66-7.70 (m, 1 H), 7.85-7.88 (m, 2 H), 7.99 (dd, J$_{HF}$=9.0, J$_{HH}$=5.1 Hz, 1 H).

HRMS (ESI) calcd for C$_{21}$H$_{22}$BrFN$_3$O$_2$ [M+H]$^+$ 446.0874, found 446.0880.

The invention claimed is:

1. A compound selected from the group consisting of:

4-(2-Amino-ethoxy)-3-(4-bromo-phenyl)-7-fluoro-2H-isoquinolin-1-one, 4-(2-Amino-ethoxy)-3-(3-bromo-4-morpholin-4-yl-phenyl)-7-fluoro-2H-isoquinolin-1-one, 4-(2-Amino-ethoxy)-3-(4-chloro-phenyl)-7-fluoro-2H-isoquinolin-1-one, 4-(2-Amino-ethoxy)-3-(4-bromo-phenyl)-7,8-difluoro-2H-isoquinolin-1-one, 4-(2-Amino-ethoxy)-3-(4-chloro-3-methyl-phenyl)-7-fluoro-2H-isoquinolin-1-one, 4-(2-Amino-ethoxy)-3-(3,4-dichloro-phenyl)-7-fluoro-2H-isoquinolin-1-one and 4-(2-Amino-ethoxy)-7-fluoro-3-(3-fluoro-4-methoxy-phenyl)-2H-isoquinolin-1-one.

2. A pharmaceutical composition comprising a therapeutically effective amount of a compound as defined in claim 1, and at least one pharmaceutically acceptable excipient, carrier or diluent.

3. A pharmaceutical composition according to claim 2, further comprising one or more chemotherapeutic agents.

4. A pharmaceutical composition according to claim 3, wherein the chemotherapeutic agent is an alkylating agent.

5. A pharmaceutical composition according to claim 4, wherein the alkylating agent is temozolomide.

6. A product comprising a compound as defined in claim 1, and one or more chemotherapeutic agents, as a combined preparation for simultaneous, separate or sequential use in anticancer therapy.

7. A product according to claim 6, wherein the chemotherapeutic agent is an alkylating agent.

8. A product according to claim 7, wherein the alkylating agent is temozolomide.

9. A process for the preparation of a compound of formula (I)

49

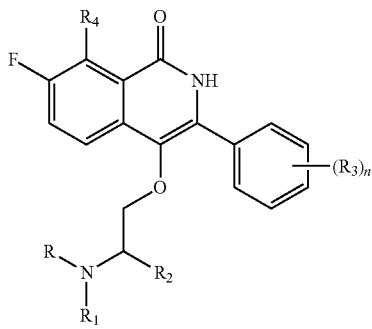

(I)

wherein

R and $R_1$ are independently hydrogen or an optionally substituted group selected from linear or branched $C_1$-$C_6$ alkyl, $C_3$-$C_7$ cycloalkyl and heterocyclyl, or, taken together with the nitrogen atom to which they are bonded, form an optionally substituted heterocycle;

$R_2$ is hydrogen or an optionally substituted group selected from linear or branched $C_1$-$C_6$ alkyl and $C_3$-$C_7$ cycloalkyl;

$R_3$ is fluorine, chlorine, bromine, cyano, or an optionally substituted group selected from linear or branched $C_1$-$C_6$ alkyl, $C_1$-$C_6$ alkoxy, polyfluorinated $C_1$-$C_6$ alkyl, polyfluorinated $C_1$-$C_6$ alkoxy, heterocyclyl, aryloxy, arylamino, $C_1$-$C_6$ alkylsulphonyl; or $R_3$ may be represented by a dioxolyl, dioxinyl or dioxepinyl ring, fused with the phenyl ring;

$R_4$ is hydrogen or fluorine, and when $R_4$ is hydrogen, n is a number between 1 and 5;

when $R_4$ is fluorine, n is a number between 0 and 5;

which comprises:

step 1) protecting a compound of formula (II):

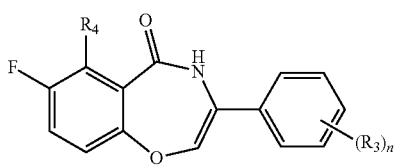

II wherein $R_3$ and R4 and n and as defined above with a compound of formula PG-X (III), wherein PG is a suitable protecting group and X is a suitable leaving group;

step 2) rearranging the resultant compound of formula (IV):

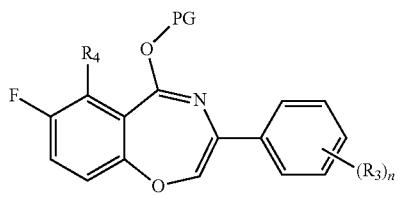

IV wherein $R_3$, $R_4$, n and PG are as defined above;

50 step 3) alkylating the resultant compound of formula (V):

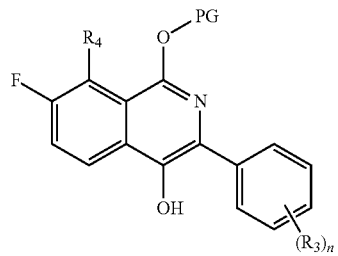

V wherein $R_3$, $R_4$, and PG are as defined above, with a compound of formula (VI):

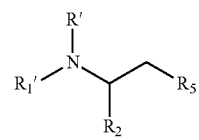

VI wherein $R_2$ is as defined above; R' and $R_1$' have the same meaning of R and $R_1$ but can also be independently $COOR_6$, wherein $R_6$ is an optionally substituted linear or branched $C_1$-$C_6$ alkyl; and $R_5$ is a suitable group;

step 4) deprotecting the resultant compound of formula (VII):

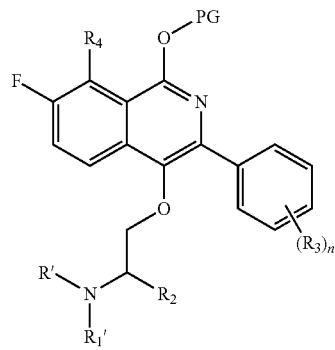

VII wherein R', $R_1$', $R_2$, $R_3$, $R_4$, n and PG are as defined above, so as to obtain a compound of formula (I), as defined above;

optionally converting a compound of formula (I) into a different compound of formula (I); and/or converting a compound of formula (I) into a pharmaceutically acceptable salt thereof or converting a salt into a free compound of formula (I);

moreover, optionally converting a compound of formula (II) or formula (IV) or formula (V) or formula (VII) into a corresponding compound of formula (II) or formula (IV) or formula (V) or formula (VII), respectively.

10. The process according to claim 9, for the preparation of a compound selected from the group consisting of:

4-(2-Amino-ethoxy)-3-(4-bromo-phenyl)-7-fluoro-2H-isoquinolin-1-one, 4-(2-Amino-ethoxy)-7-fluoro-3-(3-trifluoromethyl-phenyl)-2H-isoquinolin-1-one, 4-(2-Amino-ethoxy)-3-(3-bromo-4-morpholin-4-yl-phenyl)-7-fluoro-2H-isoquinolin-1-one, 4-(2-Amino-ethoxy)-3-(3-bromo-phenyl)-7-fluoro-2H-isoquinolin-1-one,
4-(2-Aminoethoxy)-7-fluoro-3-(4-pyrrolidin-1-yl-phenyl)-2H-isoquinolin-1-one,
4-(2-Amino-ethoxy)-3-(4-chloro-phenyl)-7-fluoro-2H-isoquinolin-1-one,
4-(2-Amino-ethoxy)-7-fluoro-3-(4-fluoro-phenyl)-2H-isoquinolin-1-one,
3-[4-(2-Amino-ethoxy)-7-fluoro-1-oxo-1,2-dihydro-isoquinolin-3-yl]-benzonitrile,
4-(2-Amino-ethoxy)-3-(4-bromo-phenyl)-7,8-difluoro-2H-isoquinol in- 1-one,
4-(2-Amino-ethoxy)-3-(4-chloro-3-methyl-phenyl)-7-fluoro-2H-isoquinolin-1-one,
4-(2-Amino-ethoxy)-3-(3,4-dichloro-phenyl)-7-fluoro-2H-isoquinolin-1-one,
4-(2-Amino-ethoxy)-3-(3,4-difluoro-phenyl)-7-fluoro-2H-isoquinolin-1-one,
4-(2-Amino-ethoxy)-3-(3-bromo-4-pyrrolidin-1-yl-phenyl)-7-fluoro-2H-isoquinolin-1-one,
4-(2-Amino-ethoxy)-3-(2,3-dihydro-benzo[1,4]dioxin-6-yl)-7-fluoro-2H-isoquinol in-1-one,
4-(2-Amino-ethoxy)-3-benzo [1,3]dioxol-5-yl-7-fluoro-2H-isoquinol in-1-one,
4-(2-Amino-ethoxy)-7-fluoro-3 -(3 -fluoro-4-methoxy-phenyl)-2H-isoquinolin- 1-one;
or a pharmaceutically acceptable salt thereof.

* * * * *